② United States Patent [19]
Anderson et al.
[11] Patent Number: 4,845,129
[45] Date of Patent: Jul. 4, 1989

[54] DIARYL SUBSTITUTED CYCLOPENTANE AND CYCLOPENTENE DERIVATIVES

[75] Inventors: Robert C. Anderson, Lake Hopatcong; William J. Houlihan, Mountain Lakes; Howard C. Smith, Plainsboro; Edwin B. Villhauer, Morristown, all of N.J.

[73] Assignee: Sandoz Pharm. Corp., E. Hanover, N.J.

[21] Appl. No.: 167,766

[22] Filed: Mar. 14, 1988

[51] Int. Cl.[4] .................. A61K 31/18; C07C 149/273

[52] U.S. Cl. .................................. 514/600; 514/605; 514/640; 514/646; 514/647; 514/676; 514/684; 514/708; 514/709; 514/710; 514/712; 514/713; 514/716; 514/719; 564/79; 564/83; 564/95; 564/99; 564/256; 564/265; 564/307; 564/440; 564/441; 564/442; 564/443; 568/29; 568/30; 568/31; 568/33; 568/36; 568/37; 568/43; 568/44; 568/49; 568/62; 568/306; 568/303; 568/644; 568/645; 568/646

[58] Field of Search .............. 568/644, 330, 306, 644, 568/645, 646, 62, 49, 44, 43, 37, 36, 33, 31, 30, 29; 564/79, 83, 443, 95, 99, 256, 442, 441, 265, 307; 514/600, 605, 640, 646, 647, 684, 676, 708, 709, 710, 712, 713, 716, 719

[56] References Cited

U.S. PATENT DOCUMENTS 2,864,868 12/1958 Bader .............................. 568/644

FOREIGN PATENT DOCUMENTS 0257921 3/1988 European Pat. Off. .

OTHER PUBLICATIONS

Allen et al., *J. Am. Chem. Soc.*, vol. 77, No. 8, pp. 2315-2317, (1955).

Doyama et al., *Chemical Abstracts*, vol. 106, No. 175799b, (1987).

Khand et al., *Chemical Abstracts*, vol. 90, No. 86801e, (1979).

*Primary Examiner*—Bruce Gray
*Attorney, Agent, or Firm*—Gerald D. Sharkin; Robert S. Honor; Joseph J. Borovian

[57] ABSTRACT

The invention discloses certain diaryl substituted cyclopentane and cyclopentene derivatives useful as PAF inhibitors, pharmaceutical compositions containing said compounds as an active ingredient thereof and a method of using such compositions for inhibiting PAF-induced blood platelet aggregation, PAF-mediated broncho-constriction and extravasation, PAF-induced hypotension, PAF-induced ischemic bowel disease and PAF-mediated, endotoxin induced lug injury.

8 Claims, No Drawings

DIARYL SUBSTITUTED CYCLOPENTANE AND CYCLOPENTENE DERIVATIVES

The present invention relates to certain diaryl substituted cyclopentane and cyclopentene derivatives and to their use as platelet activating factor (PAF) receptor antagonists and as inhibitors of PAF-induced blood platelet aggregation. The invention also relates to pharmaceutical compositions containing the afore-mentioned compounds as an active ingredient thereof and to the method of using such compositions for inhibiting PAF-mediated bronchoconstriction and extravasation, PAF-induced hypotension, PAF-involved ischemic bowel disease and PAF-mediated, endotoxin-induced lung injury.

Blood platelets, also called thrombocytes, are well recognized as important cellular elements that circulate in the blood. Their role is to staunch bleeding by forming clots in broken blood vessels, i.e., they are nature's corks. They have, however, been implicated in a variety of immunologically mediated forms of tissue injury. Their participation in these processes involved the release of platelet activating factor (PAF) which in turn interacts with the platelets, inducing aggregation and secretion of granular constituents. As a further consequence of platelet activation, there may result a fatal reaction consisting of acute pulmonary hypertension, right heart dilation, systemic hypotension, significant increases in pulmonary vascular resistance, a decrease in dynamic lung compliance and often complete pulmonary apnea. More recently, evidence has been obtained which appears to implicate platelet activating factor in the formation of fibromuscular lesions of the arterial walls of the aorta and coronary arteries, thereby contributing to the development of atherosclerosis. Further, the possible role of PAF in ischemic bowel disease, particularly necrotizing enterocolitis (NEC) has recently been described, thereby implicating PAF in the development of disorders leading to bowel necrosis. Still further, evidence has been obtained which supports the hypothesis that PAF is an important mediator of endotoxin-induced lung injury, -pulmonary hypertension, -hypoxemia and -reduced cardiac output.

The existence of platelet activating factor was proposed in an article by Henson, P. M., Journal of Experimental Medicine 131, 287 (1970). However, due to the limited quantities of material available for study, great difficulty was encountered in defining the chemical structure and biochemical activity of PAF.

One of the earlier reports on the chemical nature of PAF was that of Benveniste, J., Nature 249, 581 (1974), wherein the physiochemical characteristics of PAF were reported. A later study of Benveniste, J. et al., Nature 269, 170 (1977) reported on the purification of PAF isolated by successive thin layer chromatography. A more recent study by Hanahan, et al. in the J. of Biol. Chem. 225:5514–5516 (June 1980) confirmed that the compounds, 1-0-alkyl-2-acetyl-sn-glyceryl-3-phosphoryl-choline (AGEPC), and PAF are one and the same composition. Since that time, many research endeavors have been directed to the synthesis of compounds structurally related to that of PAF in an effort to uncover compounds useful in the inhibition of platelet activating factor.

The essence of the present invention is the discovery that certain diaryl substituted cyclopentane and cyclopentene derivatives of formula I:

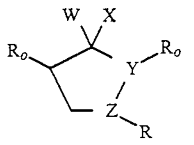

I where

W is hydrogen; $C_1$–$C_5$ alkyl or $C_3$–$C_6$alkenyl; and

X is $OR_1$ or $SR_1$ where $R_1$ is hydrogen, $C_1$–$C_5$alkyl or $C_3$–$C_6$alkenyl; or $NR_1R_1$, where each $R_1$, independently, is as defined above; with the proviso that when W is other than hydrogen, then X is $OR_1$;

or W and X, together with the carbon atom to which they are attached, are C═O or C═$NOR_1$, where $R_1$ is as defined above;

Y-Z is C═C or CH—CH;

R is hydrogen or $C_1$–$C_5$alkyl; with the proviso that when Y-Z is C═C, then R is hydrogen; and each Ro, independently, is a group of the formula

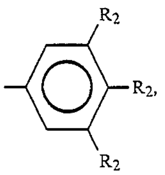

where each $R_2$ is, independently, hydrogen; $NO_2$; halo; $OR_3$, where $R_3$ is $C_1$–$C_5$alkyl; $SR_4$; $SOR_4$; $SO_2R_4$; $NHSO_2R_4$; $NR_4R_4$; $NR_4SO_2R_4$ or $NHSO_2NR_4R_4$, were each $R_4$ is $C_1$–$C_5$alkyl or $C_3$–$C_6$ alkenyl; with the proviso that only one $R_2$ can be a significance selected from hydrogen, $NO_2$, halo, $SR_4$, $SOR_4$, $SO_2R_4$, $NHSO_2R_4$, $NR_4R_4$, $NR_4SO_2R_4$ and $NHSO_2NR_4R_4$, and their pharmaceutically acceptable acid addition salts, where such may exist, are useful as PAF receptor antagonists and as inhibitors of PAF-induced blood platelet aggregation.

Included among the compounds of formula I are the compounds of subclass Ia:

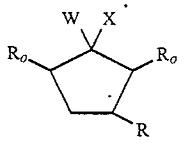

Ia where W, X, R and each Ro are as defined above; and their pharmaceutically acceptable acid addition salts, where such may exist.

The preferred compounds of subclass Ia are compounds of formula Ia':

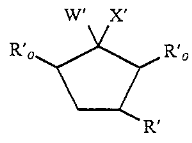

Ia' where

W' is hydrogen or $C_1$–$C_5$alkyl;

and X' is $OR'_1$ or $NR'_1R'_1$ where $R'_1$ is hydrogen or $C_1$–$C_5$alkyl; with the proviso that when W' is other than hydrogen, then X' is $OR'_1$;

or W' and X', together with the carbon atom to which they are attached, are C═O or C═NOR'$_1$, where $R'_1$ is as defined above;

R' is hydrogen or $C_1$–$C_3$alkyl;

and each $R'_o$, independently, is a group of the formula

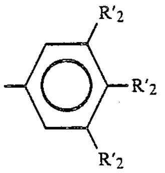

where $R_3$ is as defined above; and their pharmaceutically acceptable acid addition salts, where such may exist.

The more preferred compounds of subclass Ia are compounds of formula Ia'':

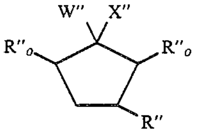

Ia'' where

W'' is hydrogen or $C_1$–$C_3$alkyl;

and X'' is $OR''_1$ or $NR''_1R''_1$ where $R'_1$ is hydrogen or $C_1$–$C_3$ alkyl; with the proviso that when W'' is other than hydrogen, then X'' is $OR''_1$;

or W'' and X'', together with the carbon atom to which they are attached, are C═O or C═NOR''$_1$ where $R''_1$ is as defined above;

R'' is hydrogen; methyl or ethyl; and the $R''_o$'s are the same and represent a group of the formula

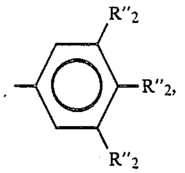

$OR'_3$ where $R'_3$ is $C_1$–$C_3$alkyl; and their pharmaceutically acceptable acid addition salts, where such may exist.

The even more preferred compounds of subsclass Ia are compounds of formula Ia''':

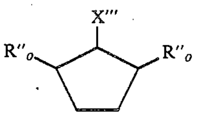

Ia''' where X''' is $OR''_1$ where $R''_1$ is as defined above; and the Ro's are the same and represent a group of the formula

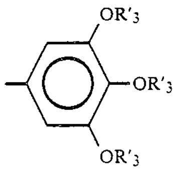

as defined above.

Also included among the compounds of formula I are the compounds of subclass Ib:

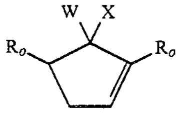

Ib where W, X and each Ro are as defined above, and their pharmaceutically acceptable acid addition salts, where such may exist.

The preferred compounds of subclass Ib are compounds of formula Ib'

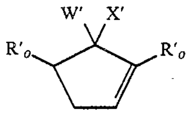

Ib' where W', X' and each Ro' are as defined above and their pharmaceutically acceptable acid addition salts, where such may exist.

The more preferred compounds of subclass Ib are compounds of formula Ib'':

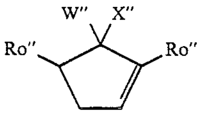

Ib'' where W'', X'' and each Ro'' are as defined above; and their pharmaceutically acceptable acid addition salts, where such may exist.

The even more preferred compounds of subclass Ib are compounds of formula Ib'':

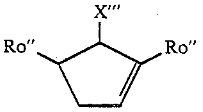

Ib'' where X'' and the Ro'''s are as defined above.

The compounds of subclass Ib where W and X, together with the carbon atom to which they are attached, are C═O and each $R_o$, independently, is a group of the formula

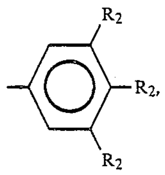

where each $R_2$, independently, is hydrogen, $NO_2$, halo or $OR_3$, where $R_3$ is as defined above and the foregoing proviso applies, may be prepared by a six-step reaction as set forth below:

STEP 1

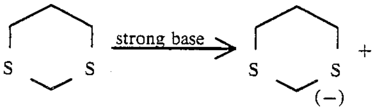

(II) (II-A)

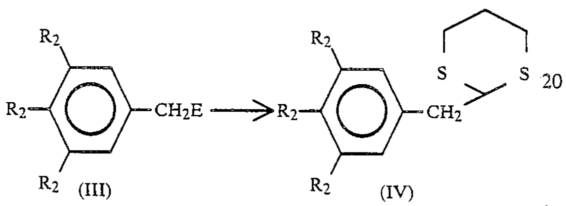

(III) (IV)

where E is halide (e.g., bromide, iodide or chloride) and the $R_2$'s are as defined above.

STEP 2

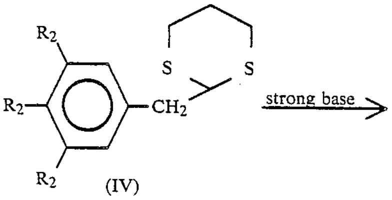

(IV)

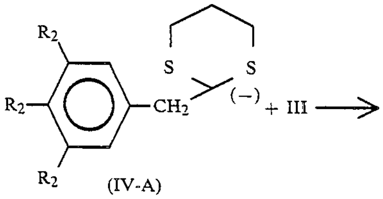

(IV-A)

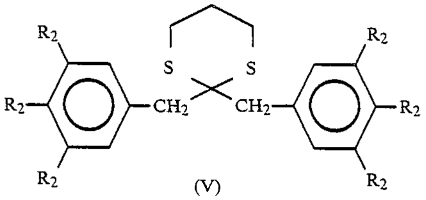

(V)

where the $R_2$'s are as defined above.

STEP 3

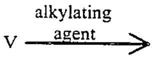

-continued

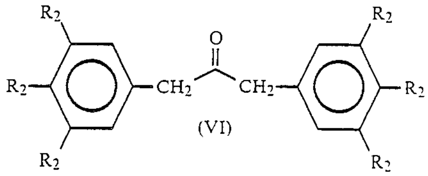

(VI)

where the $R_2$'s are as defined above.

STEP 4

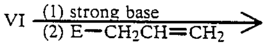

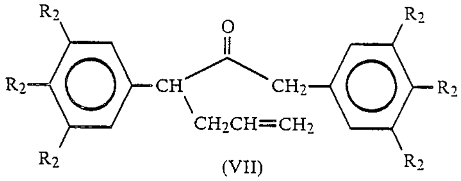

(VII)

where E and the $R_2$'s are as defined above.

STEP 5

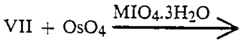

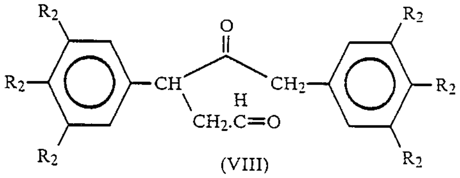

(VIII)

where M is an alkali metal and the $R_2$'s are as defined above.

STEP 6

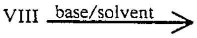

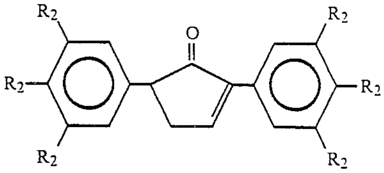

(IX)

where the $R_2$'s are as defined above.

With respect to the individual steps, the first part of Step 1 involves the deprotonation of the compound of formula II, viz., 1,3-dithiane, with a strong base such as t-butyl lithium or lithium diisopropylamide to yield the 1,3-dithiane compound in deprotonated form, i.e., the compound of formula II-A. The second part of Step 1 involves the reaction of the compound of formula II-A with a benzylic halide of formula III to yield a compound of formula IV. As to reaction conditions, both parts of Step 1 are conveniently carried out in an inert, organic solvent, e.g., a cyclic ether such as tetrahydrofuran at a temperature of from −78° C. to 50° C. for a period of between 30 minutes and 12 hours.

Step 2 involves analogous reactions to that described above in Step 1. Thus, the first part of Step 2 involves the deprotonation of a compound of formula IV with a strong base such as t-butyl lithium or lithium diisopropylamide to yield a compound of formula IV-A. The second part of Step 2 involves the reaction of a compound of formula IV-A with a compund of formula III to yield a thioketal compound of formula V. As to reaction conditions, they are identical to those described above in Step 1.

As to Step 3, it involves the conversion of a thioketal compound produced in Step 2, i.e., a compound of formula V, to a ketone compound of formula VI. The conversion is typically carried out in the presence of a mixture of mercury salts, e.g., a mixture of mercuric oxide and mercuric chloride, a mixture of copper salts, e.g., a mixture of cupric oxide and cupric chloride or, alternatively, in the presence of a halogenating agent such as N-bromosuccinimide or N-chlorosuccinimide, or an alkylating agent such as iodomethane. Additionally present is an aqueous mixture of an inert, organic solvent, e.g., acetone and water, a lower alkyl nitrile such as acetonitrile and water, a polar, aprotic solvent such as dimethylsulfoxide and water, or a lower alkanol such as methanol and water. The conversion reaction may optionally contain a weak, inorganic base such as sodium carbonate or calcium carbonate and may be conducted at a temperature of between 0° and 100° C. for a period of between 30 minutes and 72 hours.

In Step 4, a ketone compound produced in Step 3, i.e., a compound of formula VI, is reacted with a strong base such as lithium diisopropylamide in the presence of an inert, organic solvent, e.g., a cyclic ether such as tetrahydrofuran or a lower dialkyl ether such as diethyl ether, at a temperature of between $-100°$ and 50° C. for a period of between 30 minutes and 3 hours. An allylic halide is then gradually added and the reaction proceeds for a period of between 15 and 60 minutes to yield an olefin compound of formula VII.

Step 5 involves the cleavage of an olefin compound produced in Step 4; i.e., a compound of formula VII, by reaction with a stoichiometric or catalytic amount of an alcoholic (e.g., t.-butanol)osmium tetraoxide solution and an alkali metal periodate such as sodium periodate in the presence of an aqueous mixture of an inert, organic solvent, e.g., a cyclic ether such as tetrahydrofuran and water, or a lower dialkyl ether such as diethyl ether and water. The cleavage is conducted at a temperature of between 0° and 40° C. for a period of between 30 minutes and 24 hours to yield a compound of formula VIII.

The last step, viz., Step 6, is concerned with the conversion of a compound produced in Step 5, i.e., a compound of formula VIII, to a cyclopentenone compound of formula IX by reaction with a mixture of a base and a solvent for the base. Typical base/solvent combinations include sodium ethoxide/ethanol, sodium hydride/tetrahydrofuran or diethyl ether, and sodium hydroxide/benzene. Alternatively, the conversion can be conducted employing a mixture of basic alumina and an aliphatic hydrocarbon such as benzene. As to reaction conditions, the conversion is generally carried out at temperatures of from 0° to 80° C. for a period of between 30 minutes and 12 hours.

The compounds of subclass Ib where W is hydrogen, X is OH and each $R_o$, independently, is a group of the formula

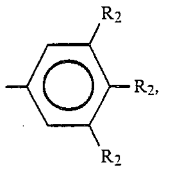

where each $R_2$, independently, is hydrogen, $NO_2$, halo or $OR_3$, where $R_3$ is as defined above and the foregoing proviso applies, may be prepared by the following reaction employing a compound of formula IX as the starting material:

REACTION A

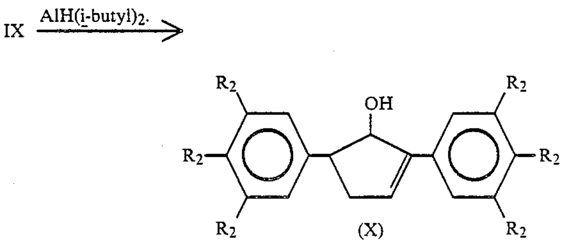

where the $R_2$'s are as defined above.

The above reaction involves the reduction of a compound of formula IX with di-i-butyl aluminum hydride to yield an alcohol of formula X. The reaction is usually carried out in the presence of an inert, organic solvent, e.q., a cyclic ether such as tetrahydrofuran, or a dialkyl ether such as diethyl ether, at a temperature of from $-78°$ C. to 30° C. for a period of between 15 minutes and 6 hours.

The compounds of subclass Ib where W is hydrogen, X is OH and each $R_o$, independently, is a group of the formula

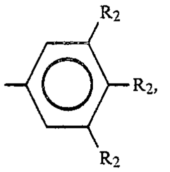

where one of the $R_2$'s is $NHSO_2R_4$ and each of the remaining $R_2$'s, independently, is hydrogen or $OR_3$, where $R_3$ is as defined above and the foregoing proviso applies may be prepared by the following reaction scheme employing a compound of formula X where one of the $R_2$'s is nitro (4'-nitro, for purposes of illustration) as the starting material:

REACTION B1

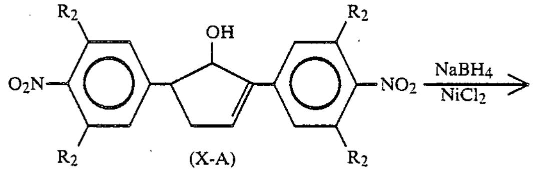

-continued

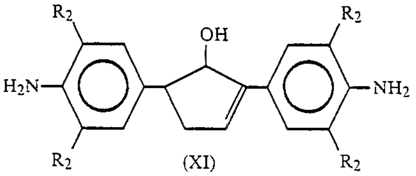

(XI)

where the $R_2$'s are hydrogen or $OR_3$, where $R_3$ is as defined above.

REACTION B2

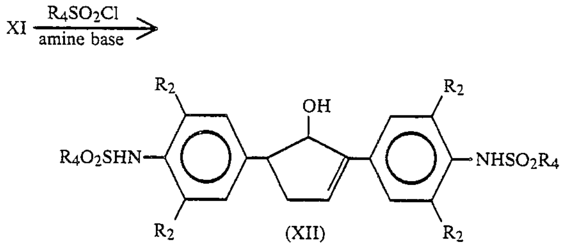

(XII)

where the $R_2$'s are hydrogen or $OR_3$, where $R_3$ is as defined above, and $R_4$ is $C_1$–$C_5$alkyl or $C_3$–$C_6$alkenyl.

Reaction B1 involves the reduction of the nitro group in a compound of formula X-A employing sodium borohydride in the presence of a nickelous chloride to yield a compound of formula XI. The reduction is typically carried out in the presence of an inert, organic solvent, e.g., a lower alkanol such as methanol at a temperature of from 0° to 50° C. for a period of between 30 minutes and 2 hours.

Reaction B2 concerns the reaction of a compound of formula XI with an alkyl or alkenyl sulfonyl chloride in the presence of an amine base such as triethylamine to obtain a compound of formula XII. The reaction is generally carried out in the presence of an inert, organic solvent, e.g., a halogenated, aliphatic hydrocarbon such as methylene chloride at a temperature of from −20° to 50° C. for a period of between 30 minutes and 8 hours.

The compounds of subclass Ib where W is hydrogen, X is OH and each $R_o$, independently, is a group of the formula

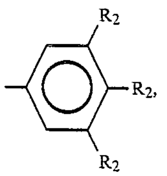

where one of the $R_2$'s is $NHSO_2NR_4R_4$ and each of the remaining $R_2$'s, independently, is hydrogen or $OR_3$, where $R_3$ is as defined above and the foregoing proviso applies may be prepared by the following reaction employing a compound of formula XI (for purposes of illustration) as the starting material:

REACTION C

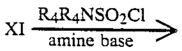

-continued

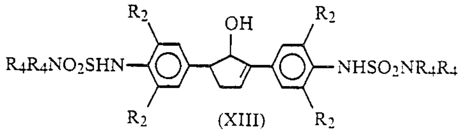

(XIII)

where the $R_2$'s are hydrogen or $OR_3$, where $R_3$ is as defined above, and the $R_4$'s are, independently, $C_1$–$C_5$alkyl or $C_3$–$C_6$alkenyl.

In the above reaction, a compound of formula XI is reacted with a sulfamoyl chloride compound in the presence of an amine base such as triethylamine to obtain a compound of formula XIII. The reaction is typically carried out in the presence of an inert, organic solvent, e.g., a halogenated, aliphatic hydrocarbon such as methylene chloride at a temperature of from 0° to 50° C. for a period of between 30 minutes and 8 hours.

The compounds of subclass Ib where W is hydrogen, X is OH and each $R_o$, independently, is a group of the formula

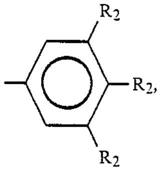

where one of the $R_2$'s is $NR_4R_4$ and each of the remaining $R_2$'s, independently, is hydrogen or $OR_3$, where $R_3$ is as defined above and the foregoing proviso applies may be prepared by the following reaction employing a compound of formula XI (for purposes of illustration) as the starting material:

REACTION D

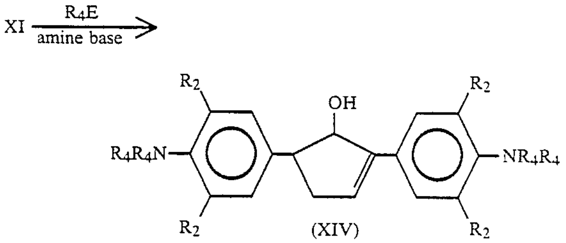

(XIV)

where the $R_2$'s are hydrogen or $OR_3$, where $R_3$ is as defined above, the $R_4$'s are independently, $C_1$–$C_5$alkyl or $C_3$–$C_6$alkenyl, and E is as defined above.

In the above reaction, an amine compound of formula XI is reacted with 4 equivalents of an alkyl or alkenyl halide in the presence of an amine base such as triethylamine to obtain a tertiary amine compound of formula XIV. The reaction is usually carried out in an inert, organi solvent, e.g., a lower alkanol such as methanol or ethanol, a cyclic ether such as tetrahydrofuran, or a dialkyl ether such as diethyl ether, or in a polar, aprotic solvent such as dimethylformamide or dimethyl sulfoxide. As to reaction conditions, the reaction is carried out at a temperature of from 0° to 80° C. for a period of between 1 and 24 hours.

When a compound of formula XIV is desired where the $R_4$'s are different (i.e., two different alkyl or alkenyl groups or one alkyl and one alkenyl group), the reaction can be carried out by the addition of two equivalents of one halide and two equivalents of a different halide or, preferably, such compounds are prepared by the sequential addition of the two different halide compounds.

The compounds of subclass Ib where W is hydrogen, X is OH and each $R_o$, independently, is a group of the formula

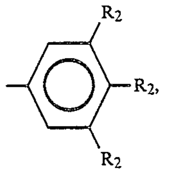

where one of the $R_2$'s is $NR_4SO_2R_4$ and each of the remaining $R_2$'s, independently, is hydrogen or $OR_3$, where $R_3$ is as defined above and the foregoing proviso applies may be prepared by the following reaction scheme employing a compound of formula XI (for purposes of illustration) as the starting material:

REACTION E1

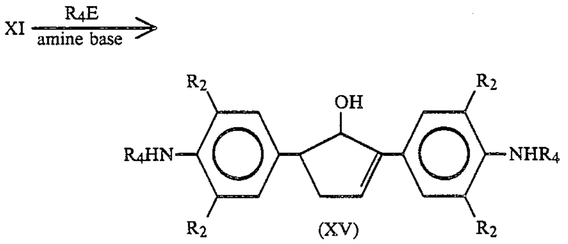

(XV)

where the $R_2$'s are hydrogen or $OR_3$, where $R_3$ is as defined above, $R_4$ is $C_1$–$C_5$alkyl or $C_3$–$C_6$alkenyl, and X is as defined above.

REACTION E2

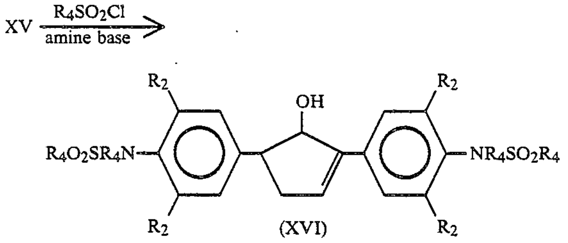

(XVI)

where the $R_2$'s are hydrogen or $OR_3$, where $R_3$ is as defined above, and the $R_4$'s are, independently, $C_1$–$C_5$alkyl or $C_3$–$C_6$alkenyl, In Reaction E1, an amine compound of formula XI is reacted with 2 equivalents of an alkyl or alkenyl halide in the presence of an amine base such as triethylamine to obtain a secondary amine compound of formula XV. The reaction is generally carried out in an inert, organic solvent, e.g., a lower alkanol such as methanol or ethanol, a cyclic ether such as tetrahydrofuran, or a dialkyl ether such as diethyl ether, or in a polar, aprotic solvent such as dimethylformamide or dimethyl sulfoxide. As to reaction conditions, the reaction is carried out at a temperature of from 0° to 80° C. for a period of between 1 and 24 hours.

As to Reaction E2, a secondary amine compound of formula XV is reacted with an alkyl or alkenyl sulfonyl chloride in the presence of an amine base such as triethylamine to obtain a tertiary sulfonamide compound of formula XVI. As to reaction conditions, they are analogous to those set forth above in Reaction B2.

The compounds of subclass Ib where W and X, together with the carbon atom to which they are attached, are C═O, and each $R_o$, independently, is a group of the formula

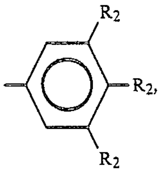

where one the $R_2$'s is $NHSO_2R_4$, $NHSO_2NR_4R_4$, $NR_4R_4$ or $NR_4SO_2R_4$ and each of the remaining $R_2$'s, independently, is hydrogen or $OR_3$, where $R_3$ is as defined above and the foregoing proviso applies may be prepared by the following reaction employing the corresponding alcohol compound (compound XII for purposes of illustration) as the starting material:

REACTION F

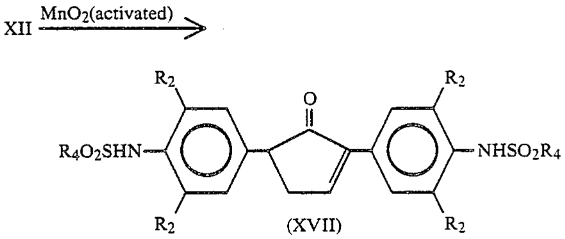

(XVII)

where the $R_2$'s are hydrogen or $OR_3$ where $R_3$ is as defined above, and $R_4$ is $C_1$–$C_5$alkyl or $C_3$–$C_6$alkenyl.

In the above reaction, a compound of formula XII is mildly oxidized employing activated manganese dioxide to obtain a keto compound of formula XVII. The oxidation is typically carried out in the presence of an inert, organic solvent, e.g., a halogenated, aliphatic hydrocarbon such as methylene chloride at a temperature of from 0° to 50° C. for a period of between 1 hour and 3 days.

The compounds of subclass Ib where W and X, together with the carbon atom to which they are attached, are C═O, and each $R_o$, independently, is a group of the formula

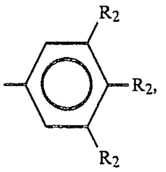

where one of the $R_2$'s is $SR_4$, and each of the remaining $R_2$'s, independently, is hydrogen or $OR_3$, where $R_3$ is as defined above and the foregoing proviso applies may be prepared by the following reaction employing a compound of formula IX where one of the $R_2$'s is halo (e.g., 4'-iodo for purposes of illustration) as the starting material:

REACTION G

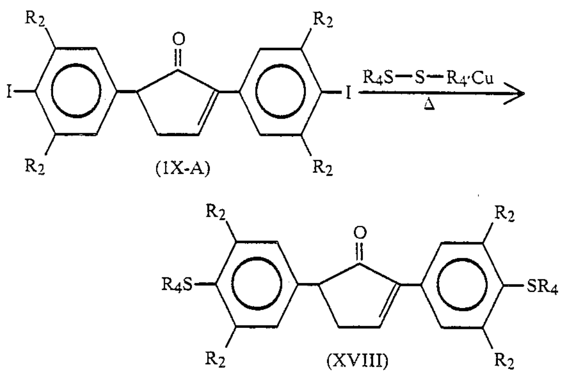

(IX-A)

(XVIII)

where the $R_2$'s are hydrogen or $OR_3$, where $R_3$ is as defined above, and $R_4$ is $C_1$–$C_5$alkyl or $C_3$–$C_6$alkenyl.

In the above reaction, a compound of formula IX-A is reacted with an alkyl or alkenyl disulfide compound in the presence of copper metal to obtain a thio compound of formula XVIII. The reaction is generally carried out in the presence of 2,4-lutidine at a temperature of from 50° to 200° C. over a period of from 1 to 24 hours.

The compounds of subclass Ib where W and X, together with the carbon atom to which they are attached, are C═O, and each $R_o$, independently, is a group of the formula

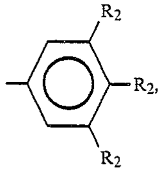

where one of the $R_2$'s is $SOR_4$, and each of the remaining $R_2$'s, independently, is hydrogen or $OR_3$, where $R_3$ is as defined above and the foregoing proviso applies may be prepared by the following reaction employing a compound of formula XVIII (for purposes of illustration) as the starting material:

REACTION H

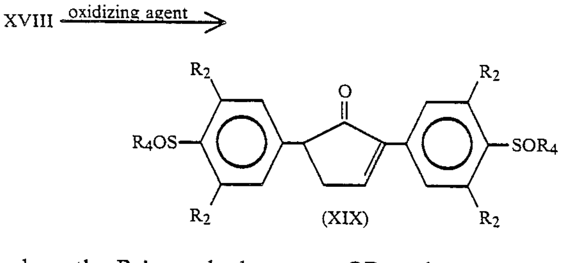

(XIX)

where the $R_2$'s are hydrogen or $OR_3$, where $R_3$ is as defined above, and $R_4$ is $C_1$–$C_5$alkyl or $C_3$–$C_6$alkenyl.

Reaction H concerns the oxidation of the thio group of a compound of formula XVIII to a sulfinyl compound of formula XIX employing one equivalent of an oxidizing agent, e.g., a peroxy carboxylic acid such as metachloroperoxybenzoic acid for each thio equivalent to be oxidized. The oxidation is generally conducted in the presence of an inert, organic solvent, e.g., a halogenated, aliphatic hydrocarbon such as methylene chloride at a temperature of from −20° to 50° C. for a period of between 1 and 60 minutes.

The compounds of subclass Ib where W and X, together with the carbon atom to which they are attached, are C═O, and each $R_o$, independently, is a group of the formula

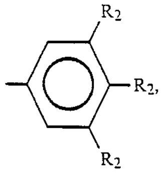

where one of the $R_2$'s is $SO_2R_4$, and each of the remaining $R_2$'s, independently, is hydrogen or $OR_3$, where $R_3$ is as defined above and the foregoing proviso applies may be prepared essentially as set forth above in Reaction H employing a compound of formula XVIII (for purposes of illustration) as the starting material and two equivalents of the oxidizing agent for each thio equivalent to be oxidized, to obtain a compound of formula XX:

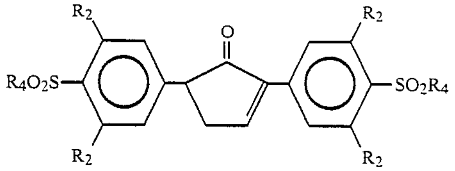

XX where the $R_2$'s are hydrogen or $OR_3$, where $R_3$ is as defined above, and $R_4$ is $C_1$–$C_5$alkyl or $C_3$–$C_6$alkenyl.

The compounds of subclass Ib where W is hydrogen, X is OH and each $R_o$, independently, is a group of the formula

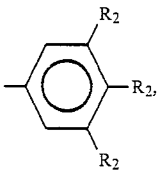

where one of the $R_2$'s is $SR_4$, $SOR_4$ or $SO_2R_4$ and each of the remaining $R_2$'s, independently, is hydrogen or $OR_3$ where $R_3$ is as defined above and the foregoing proviso applies may be prepared essentially as set forth above in Reaction A employing the corresponding keto compound (e.g., the keto compound of formula XVIII for purposes of illustration) to obtain an alcohol compound of formula XXI:

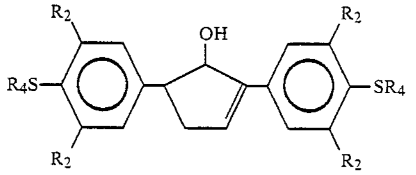

XXI where the $R_2$'s are hydrogen or $OR_3$, where $R_3$ is as defined above, and $R_4$ is $C_1$–$C_5$alkyl or $C_3$–$C_6$alkenyl.

The compounds of subclass Ib where W is hydrogen, X is $OR_1$, where $R_1$-$C_5$alkyl or $C_3$-$C_6$alkenyl and each $R_o$, independently, is a group of the formula

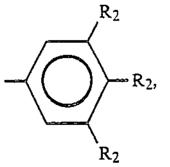

where each $R_2$, independently, is as defined above and the foregoing proviso applies, may be prepared by the following reaction:

REACTION I

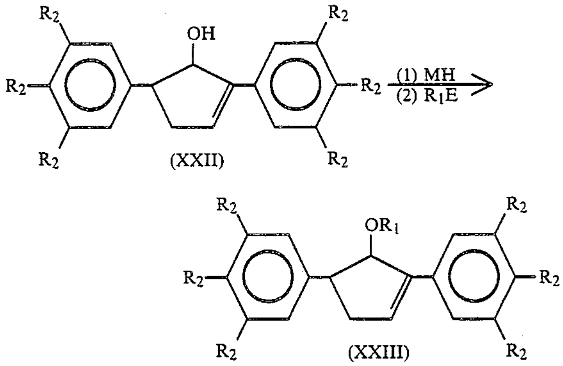

(XXII)

(XXIII)

where $R_1$ is $C_1$-$C_5$alkyl or $C_3$-$C_6$alkenyl, and M, E and the $R_2$'s are as defined above.

In the above reaction, an alcohol of formula XXII is reacted with an alkali metal hydride such as sodium hydride in the presence of an inert, organic solvent, e.g., a cyclic ether such as tetrahydrofuran, or a dialkyl ether such as diethyl ether, or a polar, aprotic solvent such as dimethylformamide at a temperature of from $-10°$ to $20°$ C. for a period of between 15 and 45 minutes. An alkyl or alkenyl halide is then added and the reaction proceeds at a temperature of from 0° to 50° C. for a period of between 1 and 5 hours to yield a compound of formula XXIII.

In the above reaction, it should be noted that when one of the $R_2$'s in the alcohol compound of formula XXII is $NHSO_2R_4$ or $NHSO_2NR_4R_4$, then two or more equivalents of the alkali metal hydride and one equivalent of the alkyl or alkenyl halide is employed in the reaction.

The compounds of subclass Ib where W is hydrogen, X is SH and each $R_o$, independently, is a group of the formula

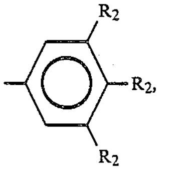

where each $R_2$, independently, is as defined above and the foregoing proviso applies may be prepared by the following reaction employing a compound of formula XXII as the starting material:

REACTION J

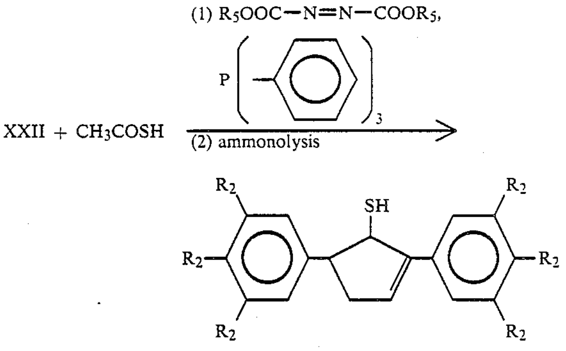

(XXIV)

where $R_5$ is $C_1$-$C_5$alkyl and the $R_2$'s are as defined above.

In the first part of the above reaction, an alcohol compound of formula XXII is reacted with thiolacetic acid in the presence of an azodicarboxylate and triphenylphosphine in an inert, organic solvent, e.g., a cyclic ether such as tetrahydrofuran, or in a polar, aprotic solvent such as dimethylformamide at a temperature of from $-78°$ C. to 50° C. for a period of between 8 hours and 3 days.

The second part involves subjecting the product produced in the first part to ammonolysis (i.e., a mixture of ammonia in water) in the optional presence of a cosolvent, e.g., a lower alkanol such as ethanol or a cyclic ether such as dioxane or tetrahydrofuran to obtain a thio compound of formula XXIV.

The compounds of subclass Ib where W is hydrogen, X is $SR_1$, where $R_1$ is $C_1$-$C_5$alkyl or $C_3$-$C_6$alkenyl and each $R_o$, independently, is a group of the formula

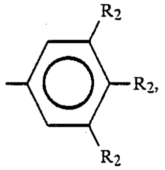

where each $R_2$, independently, is as defined above and the foregoing proviso applies may be prepared essentially as set forth above in Reaction I employing a thio compound of formula XXIV as the starting material to obtain an alkyl or alkenyl thio compound of formula XXV:

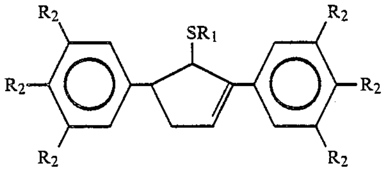

XXV where $R_1$ is $C_1$-$C_5$alkyl or $C_3$-$C_6$alkenyl and the $R_2$'s are as defined above.

The compounds of subclass Ib where W is hydrogen, X is $NH_2$, and each $R_o$, independently, is a group of the formula

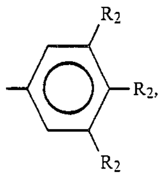

where each $R_2$, independently, is as defined above and the foregoing proviso applies may be prepared by the following reaction scheme employing a compound of formula XXII as the starting material:

REACTION K1

XXII

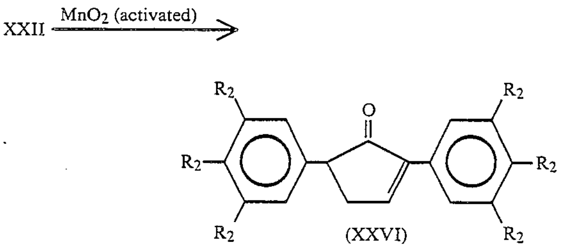

(XXVI)

where the $R_2$'s are as defined above.

REACTION K2

XXVI + $LiCNBH_3$

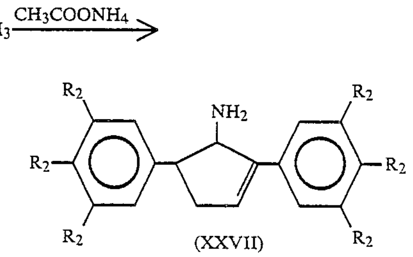

(XXVII)

where the $R_2$'s are as defined above.

Reaction K1 concerns the oxidation of a compound of formula XXII employing activated manganese dioxide to obtain a keto compound of formula XXVI. The oxidation is carried out essentially as set forth above in Reaction F.

Reaction K2 involves the reaction of a keto compound produced in Reaction K1, i.e., a compound of formula XXVI, with lithium cyanoborohydride in the presence of ammonium acetate to produce an amine compound of formula XXVII. The reaction is generally carried out in the presence of an inert, organic solvent, e.g., a lower alkanol such as methanol at a temperature of from 0° to 50° C. for a period of between 1 and 72 hours. Optionally, the reaction may be catalyzed by employing molecular sieves and/or acid such as hydrochloric acid.

The compounds of subclass Ib where W is hydrogen, X is $NHR_1$, where $R_1$ is $C_1$-$C_5$alkyl or $C_3$-$C_6$alkenyl, and each $R_o$, independently, is a group of the formula

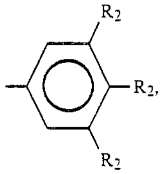

where each $R_2$, independently, is as defined above and the foregoing proviso applies may be prepared essentially as set forth above in Reaction K2, with the exception that, in place of the ammonium acetate, an equivalent amount of an alkyl or alkenyl amine is employed to obtain a compound of formula XXVIII:

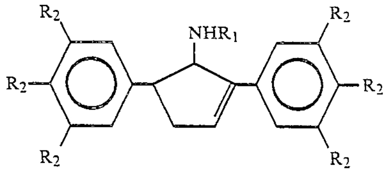

XXVIII where $R_1$ is $C_1$-$C_5$alkyl or $C_3$-$C_6$alkenyl and the $R_2$'s are as defined above.

The compounds of subclass Ib where W is hydrogen, X is $NR_1R_1$, where the $R_1$'s are $C_1$-$C_5$alkyl or $C_3$-$C_6$alkenyl, and each $R_o$, independently, is a group of the formula

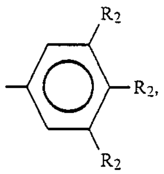

where each $R_2$, independently, is as defined above and the foregoing proviso applies may be prepared essentially as set forth above in Reaction K2 with the exception that, in place of the ammonium acetate, an equivalent of a dialkyl or dialkenyl amine is employed to obtain a compound of formula XXIX:

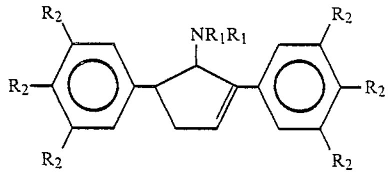

XXIX where the $R_1$'s are $C_1$-$C_5$alkyl or $C_3$-$C_6$alkenyl, and the $R_2$'s are as defined above.

When a compound of formula XXIX is desired where the $R_1$'s are different (i.e., two different alkyl or alkenyl groups or one alkyl and one alkenyl group), the reaction can be carried out employing an equivalent of a mixed dialkyl, alkyl-alkenyl or dialkenyl amine.

The compounds of subclass Ib where W and X, together with the carbon atom to which they are attached, are $C{=}NOR_1$, and each $R_o$, independently, is a group of the formula

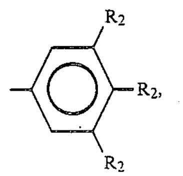

where each $R_2$ independently, is as defined above and the foregoing proviso applies may be prepared by the following reaction employing a compound of formula XXVI as the starting material:

REACTION L

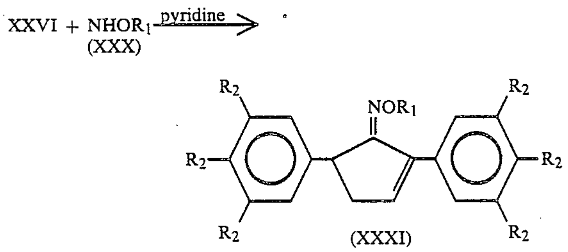

(XXXI)

where $R_1$ is hydrogen, $C_1$–$C_5$alkyl or $C_3$–$C_6$alkenyl and the $R_2$'s are as defined above.

In the above reaction, a keto compound of formula XXVI is reacted with a hydroxyl amine, an alkoxy amine or an alkenoxy amine in the presence of pyridine at a temperature of from 0° to 100° C. for a period of between 1 and 24 hours to obtain a compound of formula XXXI.

The compounds of subclass Ia where W and X, together with the carbon atom to which they are attached, are C=O, R is hydrogen and each $R_o$, independently, is a group of the formula

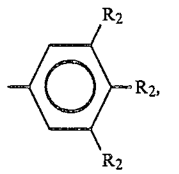

where each $R_2$, independently, is as defined above and the foregoing proviso applies may be prepared by the following reaction employing a compound of formula XXVI as the starting material:

REACTION M

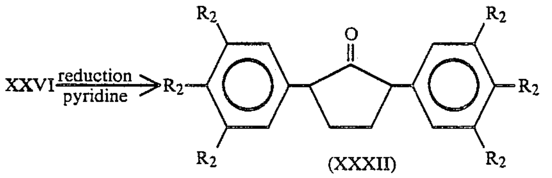

(XXXII)

where the $R_2$'s are as defined above.

In the above reaction, a cyclopentenone compound of formula XXVI is reduced employing a reducing agent such as sodium borohydride in the presence of pyridine and, optionally, a co-solvent, e.g., a cyclic ether such as tetrahydrofuran, or a dialkyl ether such as diethylether. The reduction is typically carried out at a temperature of from 0° to 50° C. for a period of between 30 minutes and 24 hours to obtain a cyclopentanone compound of formula XXXII.

The compounds of subclass Ia where W is hydrogen, X is OH, R is hydrogen and each $R_o$, independently, is a group of the formula

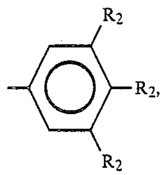

where each $R_2$, independently, is as defined above and the foregoing proviso applies may be prepared by the following reaction employing a ketone compound of formula XXXII as the starting material:

REACTION N

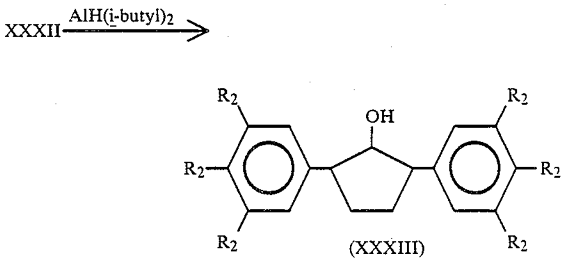

(XXXIII)

where the $R_2$'s are as defined above.

The above reaction involves the reduction of a cyclopentanone compound of formula XXXII with di-i-butyl aluminum hydride to yield an alcohol of formula XXXIII. The reaction is generally carried out in the presence of an aromatic hydrocarbon such as toluene at a temperature of from −78° to 50° C. for a period of between 1 hour and 2 days.

The compounds of subclass Ia where W is hydrogen, X is $OR_1$, where $R_1$ is $C_1$–$C_5$alkyl or $C_3$–$C_6$alkenyl, R is hydrogen and each $R_o$, independently, is a group of formula

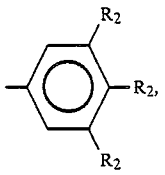

where each $R_2$, independently, is as defined above and the foregoing proviso applies may be prepared by the following reaction employing an alcohol compound of formula XXXIII as the starting material:

REACTION O

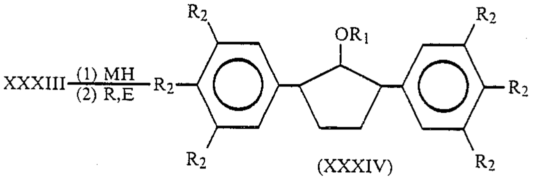

(XXXIV)

where $R_1$ is $C_1$–$C_5$alkyl or $C_3$–$C_6$alkenyl, and M, E and the $R_2$'s are as defined above.

In the above reaction, an alcohol of formula XXXIII is reacted with an alkali metal hydride in the presence of an inert, organic solvent, e.g., a cyclic ether such as tetrahydrofuran, or a dialkyl ether such as diethyl ether, or a polar, aprotic solvent such as dimethylformamide at a temperature of from −10° to 20° C. for a period of between 15 and 45 minutes. An alkyl or alkenyl halide is then added and the reaction proceeds at a temperature of from 0° to 50° C. for a period of between 1 and 5 hours to yield a compound of formula XXXIV.

It should be noted that when one of the $R_2$'s in the alcohol compound of formula XXXIII is $NHSO_2R_4$ or $NHSO_2NR_4R_4$, then two or more equivalents of the alkali metal hydride and one equivalent of the alkyl or alkenyl halide is employed in the reaction.

The compounds of subclass Ia where W is hydrogen, X is SH, R is hydrogen and each $R_o$, independently, is a group of the formula

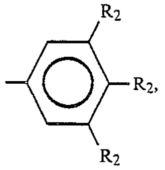

where each $R_2$, independently, is as defined above and the foregoing proviso applies may be prepared by the following reaction employing an alcohol compound of formula XXXIII as the starting material:

REACTION P

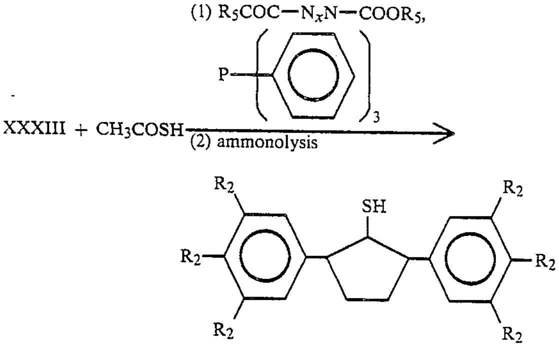

(XXXV)

where the $R_2$'s and the $R_5$'s are as defined above.

In the first part of the above reaction, an alcohol compound of formula XXXIII is reacted with thiolacetic acid in the presence of an azodicarboxylate and triphenylphosphine under the same reaction conditions set forth above in the first part of Reaction J.

The second part of the above reaction involves subjecting the product produced in the first part to ammonolysis in the optional presence of a cosolvent, e.g., a lower alkanol such as ethanol or a cyclic ether such as dioxane or tetrahydrofuran to obtain a thio compound of formula XXXV.

The compounds of subclass Ia where W is hydrogen, X is $SR_1$ where $R_1$ is $C_1$–$C_5$alkyl or $C_3$–$C_6$alkenyl, R is hydrogen and each $R_o$, independently, is a group of the formula

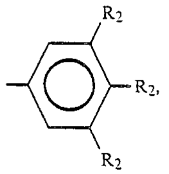

where each $R_2$, independently, is as defined above and the foregoing proviso applies may be prepared essentially as set forth above in Reaction O employing a thio compound of formula XXXV as the starting material to obtain an alkyl or alkenyl thio compound of formula XXXVI:

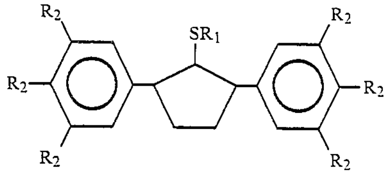

XXXVI where $R_1$ is $C_1$–$C_5$alkyl or $C_3$–$C_6$alkenyl and the $R_2$'s are as defined above.

The compounds of subclass Ia where W and X, together with the carbon atom to which they are attached, are $C{=}NOR_1$, R is hydrogen and each $R_o$, independently, is a group of the formula

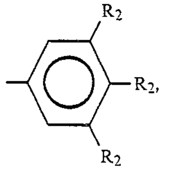

where each $R_2$, independently, is as defined above and the foregoing proviso applies may be prepared essentially as set forth above in Reaction L employing a keto compound of formula XXXII as the starting material to obtain a compound of formula XXXVII:

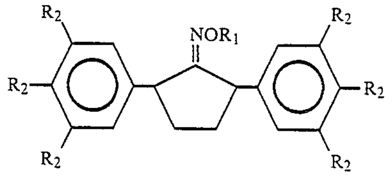

XXXVII where $R_1$ is hydrogen, $C_1$–$C_5$alkyl or $C_3$–$C_6$alkenyl and the $R_2$'s are as defined above.

The compounds of subclass Ia where W is hydrogen, X is $NH_2$, R is hydrogen and each $R_o$, independently, is a group of the formula

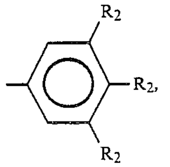

where each $R_2$, independently, is as defined above and the foregoing proviso applies may be prepared by the following reaction:

REACTION Q

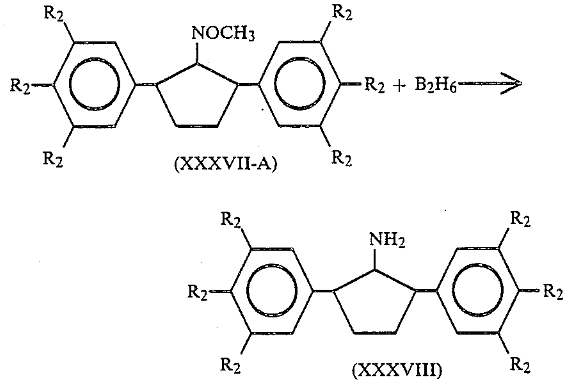

(XXXVII-A) (XXXVIII)

where the $R_2$'s are as defined above.

In the above reaction, a compound of formula XXXVII-A is reacted with diborane to obtain an amine compound of formula XXXVIII. The reaction is generally carried out in the presence of an inert, organic solvent, e.g., a cyclic ether such as tetrahydrofuran, or a dialkyl ether such as diethylether at a temperature of from 0° to 100° C. for a period of between 1 and 24 hours.

The compounds of subclass Ia where W is hydrogen, X is $NHR_1$, where $R_1$ is $C_1$–$C_5$alkyl or $C_3$–$C_6$alkenyl, R is hydrogen and each $R_o$, independently, is a group of the formula

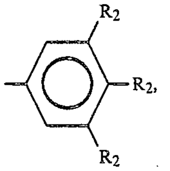

where each $R_2$, independently, is as defined above and the foregoing proviso applies may be prepared essentially as set forth above in Reaction K2 employing a compound of formula XXXII as the starting material wih the exception that, in place of the ammonium acetate, an equivalent amount of an alkyl or alkenyl amine is employed to obtain a compound of formula XXXIX:

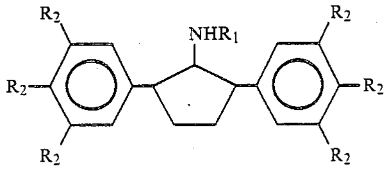

XXXIX where $R_1$ is $C_1$–$C_5$alkyl or $C_3$–$C_6$alkenyl and the $R_2$'s are as defined above.

The compounds of subclass Ia where W is hydrogen, X is $NR_1R_1$, where the $R_1$'s are $C_1$–$C_5$alkyl or $C_3$–$C_6$alkenyl, R is hydrogen and each $R_o$, independently, is a group of the formula

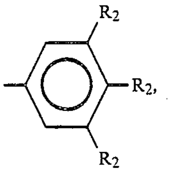

where each $R_2$, independently, is as defined above and the foregoing proviso applies may be prepared essentially as set forth above in Reaction K2 employing a compound of formula XXXII as the starting material with the exception that, in place of the ammonium acetate, an equivalent of a dialkyl or dialkenyl amine are employed to obtain a compound of formula XL:

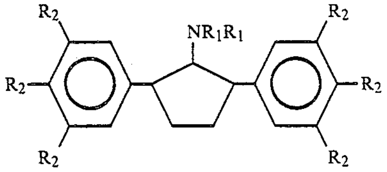

XL where the $R_1$'s are $C_1$–$C_5$alkyl or $C_3$–$C_6$alkenyl, and the $R_2$'s are as defined above.

When a compound of formula XL is desired where the $R_1$'s are different (i.e., two different alkyl or alkenyl groups or one alkyl and one alkenyl group), the reaction can be carried out employing one equivalent of a mixed dialkyl, alkyl-alkenyl or dialkenyl amine.

The compounds of subclass Ia where W and X, together with the carbon atom to which they are attached, are C═O, R is $C_1$–$C_5$alkyl and each Ro, independently, is a group of formula

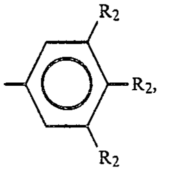

where each $R_2$, independently, is as defined above and the foregoing proviso applies may be prepared by the following reaction employing a compound of of formula XXVI as the starting material:

REACTION R

XXVI +

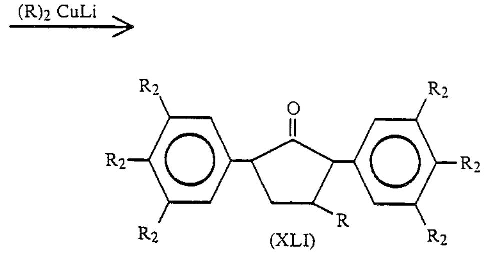

(XLI)

where R is $C_1$-$C_5$alkyl and the $R_2$'s are as defined above.

In the above reaction, a cyclopent-2-enone compound is reacted with a di-$C_1$-$C_5$alkyl copper lithium compound to obtain a cyclopentanone compound of formula XLI. The reaction is typically carried out in the presence of an inert, organic solvent, e.g., a cyclic ether such as tetrahydrofuran, a dialkyl ether such as diethyl ether, or an aliphatic hydrocarbon such as pentane, at a temperature of from −78° to 30° C. for a period of between 30 minutes and 12 hours.

The remaining compounds of subclass Ia where R is $C_1$-$C_5$alkyl and each Ro, independently, is a group of the formula

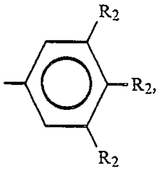

where each $R_2$, independently, is as defined above and the foregoing proviso applies may be prepared by the analogous reactions described above for preparing the corresponding compounds where R is hydrogen employing a cyclopentanone compound of formula XLI as the starting material. For example, the compounds of subclass Ia where W is hydrogen, X is OH, R is $C_1$-$C_5$alkyl and each Ro, independently, is a group of the formula

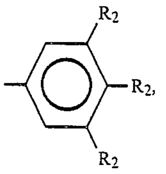

where each $R_2$, independently, is as defined above and the foregoing proviso applies may be prepared essentially as set forth above in Reaction N employing a cyclopentanone compound of formula XLI as the starting material to obtain an alcohol compound of formula XLII:

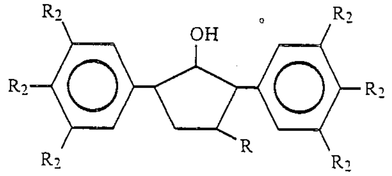

XLII where R is $C_1$-$C_5$alkyl and the $R_2$'s are as defined above.

The compounds of subclass Ia where W is other than hydrogen, X is OH, R is hydrogen and each Ro, independently, is a group of the formula

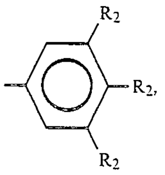

where each $R_2$, independently, is as defined above and the foregoing proviso applies may be prepared by the following reaction employing a compound of formula XXXII as the starting material:

REACTION S

XXXII +

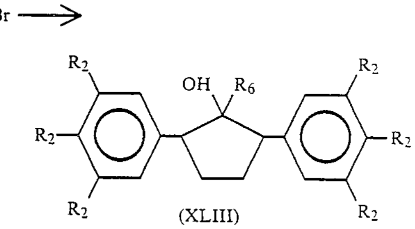

(XLIII)

where $R_6$ is $C_1$-$C_5$alkyl or $C_3$-$C_6$alkenyl and the $R_2$'s are as defined above.

In the above reaction, a cyclopentanone compound of formula XXXII is reacted with an alkyl or alkenyl magnesium bromide to obtain a compound of formula XLIII. The reaction is conducted in the presence of an inert, organic solvent, e.g., a cyclic ether such as tetrahydrofuran or a dialkyl ether such as diethyl ether at a temperature of from −78° C. to 50° C. for a period of between 1 and 24 hours.

The compounds of suclass Ia where W is other than hydrogen, X is $OR_1$, where $R_1$ is $C_1$-$C_5$alkyl or $C_3$-$C_6$alkenyl, R is hydrogen and each Ro, independently, is a group of the formula

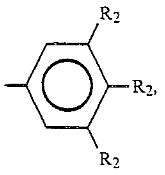

where each $R_2$, independently, is as defined above and the foregoing proviso applies may be prepared essentially as set forth above in Reaction O employing a compound of formula XLIII as the starting material to obtain a compound of formula XLIV:

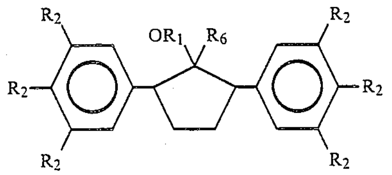

XLIV where $R_1$ and $R_6$ are $C_1$–$C_5$alkyl or $C_3$–$C_6$alkenyl and the $R_2$'s are as defined above.

It should be noted that when one of the $R_2$'s in the compound of formula XLIII is $NHSO_2R_4$ or $NHSO_2NR_4R_4$, then two or more equivalents of the alkali metal hydride and one equivalent of the alkyl or alkenyl halide is employed in the reaction.

The compounds of subclass Ia where W is other than hydrogen, X is OH, R is $C_1$–$C_5$alkyl and each Ro, independently, is a group of the formula

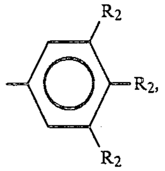

where each $R_2$, independently, is as defined above and the foregoing proviso applies may be prepared essentially as set forth above in Reaction S employing a compound of formula XLI as the starting material to obtain a compound of formula XLV:

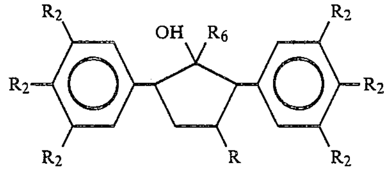

XLV where R, $R_6$ and the $R_2$'s are as defined above.

The compounds of subclass Ia where W is other than hydrogen, X is $OR_1$, where $R_1$ is $C_1$–$C_5$alkyl or $C_3$–$C_6$alkenyl, R is $C_1$–$C_5$alkyl and each Ro, independently, is a group of the formula

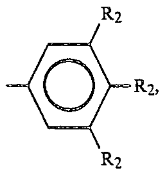

where each $R_2$, independently, is as defined above and the foregoing proviso applies may be prepared essentially as set forth above in Reaction O employed a compound of formula XLV as the starting material to obtain a compound of formula XLVI:

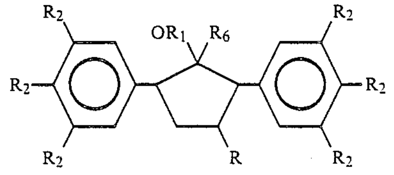

XLVI where $R_1$ and $R_6$ are $C_1$–$C_5$alkyl or $C_3$–$C_6$alkenyl, and R and the $R_2$'s are as defined above.

It should be noted that when one of the $R_2$'s in the compound of formula XLV is $NHSO_2R_4$ or $NHSO_2NR_4R_4$, then two or more equivalents of the alkali metal hydride and one equivalent of the alkyl or alkenyl halide is employed in the reaction.

The compounds of subclass Ib where W is other than hydrogen, X is OH and each Ro, independently, is a group of the formula

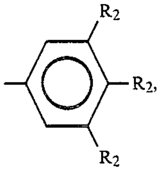

where each $R_2$, independently, is as defined above and the foregoing proviso applies may be prepared essentially as set forth above in Reaction S employing a compound of formula XXVI as the starting material to obtain a compound of formula XLVII:

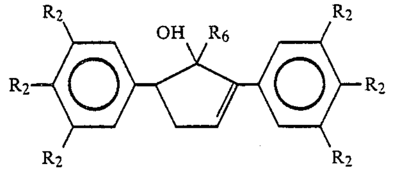

XLVII where $R_6$ and the $R_2$'s are as defined above.

The compounds of subclass Ib where W is other than hydrogen, X is $OR_1$, where $R_1$ is $C_1$–$C_5$alkyl or $C_3$–$C_6$alkenyl and each Ro, independently, is a group of the formula

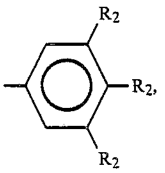

where each $R_2$, independently, is as defined above and the forgoing proviso applies may be prepared essentially as set forth above in Reaction O employing a compound of formula XLVII as the starting material to obtain a compound of formula XLVIII:

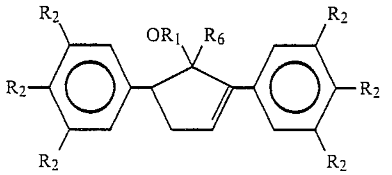

XLVIII where $R_1$ and $R_6$ are $C_1$–$C_5$alkyl or $C_3$–$C_6$alkenyl and the $R_2$'s are as defined above.

It should be noted that when one of the $R_2$'s in the compound of formula XLVII is $NHSO_2R_4$ or $NHSO_2NR_4R_4$, then two or more equivalents of the alkali metal hydride and one equivalent of the alkyl or alkenyl halide is employed in the reaction.

As to the particular starting materials of formula II or XXX, they are known and obtained by methods described in the literature.

The product of each reaction may, if desired, be purified by conventional techniques such as recrystallization (if a solid), column chromatography, preparative thin layer chromatography, gas chromatography (if sufficiently volatile), or fractional distillation under high vacuum (if sufficiently volatile). Often, however, the crude product of one reaction may be employed in the following reaction without purification.

As is evident to those skilled in the art, all of the compounds of formula I can exist as stereiosomers and such stereoisomers and their enantiomers are contemplated as being included within the scope of this invention.

All of the compounds of formula I are useful as platelet activating factor inhibitors as indicated by their ability to inhibit platelet activating factor (PAF)-induced human platelet aggregation in vitro according to the Platelet Aggregation Inhibition Assay test (PAIA test) as follows:

Human subjects are kept aspirin free for one week and fasted overnight. Platelet rich plasma (PRP) is prepared by centrifugation (200×g.) of freshly drawn blood, anti-coagulated with 0.38% sodium citrate (final concentration). Platelet count is adjusted to 250,000 per μl using platelet poor plasma (PPP) obtained by a second centrifugation (700×g.) of the blood sample. An aliquot (0.38 ml) of the PRP is dispensed into cuvettes and maintained at room temperature (22° C.) until used (but for not more than two hours). The PRP-containing cuvettes are incubated at 37° C. and stirred at 900 rpm within a Payton Aggregometer which is activated to follow the light deflection pattern prior to the addition of the test compound. The test compound (dissolved in a suitable solvent mixture which does not influence platelet aggregation) is then added to a PRP-containing cuvette in an amount sufficient to provide a final concentration of 100 μM. Between one and two minutes after the addition of the test compound, the aggregation inducing agent (C-16 PAF-Sandoz-Hanover), dissolved in a buffer consisting of 0.01M Tris-Tyrodes buffer with 0.25% bovine serum albumin (pH 7.4), is added to the PRP-containing cuvettes in an amount predetermined to give a consistent aggregation response (either 0.1 μM or 0.01 μM). All aggregations are allowed to proceed for 6 minutes from the addition of the inducing agent. The aggregation response is quantitated by determining the area under the curve (AUC). The AUC calculated for the inducing agent alone is considered to be one hundred percent. The potential percent inhibition of the aggregation response is characterized by dividing the AUC generated in the presence of the compound by the AUC of the inducing agent alone, multiplying by 100 and then subtracting from 100. The compounds demonstrating greater than 50% inhibition at 100 μm are evaluated at lower concentrations to generate an $IC_{50}$ (50% inhibitory concentration) value.

Moreover, it has been found that all of the compounds of formula I are useful as platelet activating factor receptor antagonists as indicated by their ability to inhibit specific binding of [$^3$H]-PAF to platelets according to the Human Platelet PAF Receptor Assay test (Test A) as follows:

Human blood is obtained by venipuncture of healthy, human donors into an anti-coagulant mixture containing 3.15% of trisodium citrate and 20 μg/ml of Prostaglandin $I_2$ ($PGI_2$) in a ratio of blood to anti-coagulant of 9:1. Platelet rich plasma (PRP) is prepared by centrifugation (250×g) of the blood for 20 minutes at room temperature. The PRP is then centrifuged (900°g) for 10 minutes at room temperature and the platelet pellet is washed two times with Tris-Tyrode's (TT) solution having a pH of 7.4 and containing 0.25% bovine serum albumin (BSA), and to which has been added $PGI_2$ at a final concentration of 0.3 g/ml. The platelets are resuspended at 350,000 μl in TT/BSA containing 1.4 mM $CaCl_2.2H_2O$ and 0.7 mM $MgCl_2.6H_2O$. All of the tests are conducted in duplicate and each of the test compounds is evaluated at concentrations of 100, 500, 1 and 0.1 μM. For each determination, the following solutions are mixed:

500 μl of the above-described platelets;

10 μl of [$^3$H]-PAF (40,000 counts per minute (cpm) to a final concentration of 1.5 μM); and either 10 μl of the test compound at 50× the desired final concentration, 10 μl of vehicle (total bound), or 10 μl of $1.85\times10^{-5}$M cold PAF (non-specifically bound).

Each mixture is allowed to incubate at room temperature for one hour, after which time the reaction is terminated by the addition of 500 μl of ice cold TT/BSA and centrifugation (900×g) at 4° C. for 10 minutes. The resultant supernatant is aspirated into scintillation vials and the pellet is washed with 250 ml. of ice cold TT/BSA and centrifuged (900×g) at 4° C. for 10 minutes. The supernatants are then aspirated into the same scintillation vials as before and 10 ml. of Scintiverse II (a liquid scintillation cocktail) is added to and mixed therewith. The pellets are resuspended in 500 μl of Scintiverse II and mixed well. An additional 2 ml. of Scintiverse II is then added to the vials and, after mixing, the vials are counted for 1 minute in a liquid scintillation spectrometer. The amount of specific binding is calculated as the difference in cpm between the total bound [$^3$H]-PAF and non-specifically bound [$^3$H]-PAF. The percent inhibition of specific binding is determined by dividing the cpm specifically bound in the presence of the test compound by the cpm specifically bound in total, multiplying by 100 and then subtracting from 100. An $IC_{50}$ (50% inhibitory concentration) value is generated by evaluating the test compound over the full concentration range.

Furthermore, in view of their usefulness as PAF receptor antagonists, the compounds of formula I have been found useful as inhibitors of PAF-mediated broncho-constriction, which property was evaluated by the PAF-induced Pulmonary Inflation Pressure (PIP) Increase test (Test B) as follows:

Male guinea pigs, weighing between 300 and 400 gm, are anesthetized, after which time trachea tube, carotid and jugular catheters are inserted. The test animal is then force ventilated employing a small animal Harvard respirator and the resistance to lung inflation (PIP) is measured utilizing a pressure transducer and recorder. The test compound is administered orally at 30 minutes prior to, intravenously (jugular) at 5 minutes prior to, or intraarterially at 1 to 5 minutes prior to the introduction of PAF. The PAF ($C_{18}$-Sandoz, Hanover) is dissolved in Tris-Tyrode's bovine serum albumin buffer and administered intravenously (jugular) at 100 ng/kg. Any blood pressure measurements taken are recorded from a transducer attached to the carotid catheter. Two responses are noted in the PIP recordings after the PAF is administered: (1) an immediate response which, in PAF-only treated test animals, averages out to between 70% and 80% more than the baseline PIP values. (This early response is also the greatest response and is, therefore, termed maximal PIP); and (2) the long term (at least 30 minutes) PIP response which slowly decreases to baseline. A reading at 15 minutes after the administration of PAF is termed the endpoint PIP. The effect of the test compound on the PIP response is determined by the difference between the percent increase in maximal PIP over baseline for the test animal to which has been administered PAF and the test compound compared to the test animal to which only PAF has been administered to generate an ED 50 (dose needed to effect a 50% response).

Still further, the compounds of formula I are useful as inhibitors of PAF-mediated extravasation (the extrusion of plasma from the lumen of the blood vessels into the vessel wall and surrounding tissues) measured as a function of hemoconcentration according to the PAF-induced Extravasation test (Test C) as follows:

Male guinea pigs, weighing between 300 and 400 gm, are anesthetized, after which time a femoral catheter is inserted. The test compound is administered intraarterially at one to five minutes prior to the introduction of PAF. The PAF ($C_{18}$-Sandoz, Hanover) is dissolved in Tris-Tyrode's bovine serum albumin buffer and administered intravenously (jugular) at 100 ng/kg.

To determine the hematocrit value, which is employed to index hemoconcentration and is defined as the percent of packed red blood cells in a sample of blood which is centrifuged to separate plasma from the cellular components, blood samples are collected in 50 $\mu$l heparinized hematocrit tubes. These samples are taken just prior to the injection of PAF, one minute subsequent to the injection of PAF and every two minutes thereafter until 15 minutes has lapsed subsequent to the injection of PAF. The tubes are then centrifuged and the percent of packed red blood cells (hematocrit) is measured (PAF induces a maximal increase in hematocrit at 5 to 7 minutes subsequent to the injection of PAF). The percent increase in hematocrit over the value prior to the injection of PAF is calculated. The hematocrit values obtained with the test compound are compared to the hemoconcentration values obtained with PAF alone and are expressed as percent inhibition of percent increase in hematocrit. From the values obtaine, an $ED_{50}$ is generated.

Yet still further, the compounds of formula I are useful as inhibitors of PAF-induced hypotension as measured by their ability to inhibit the lowering of blood pressure levels induced by PAF according to the following test (Test D):

Male Wistar rats, weighing approximately 300 gm, are anesthetized and their carotid arteries cannulated to enable their diastolic and systolic arterial blood pressure measurements to be recorded. PAF is then administered intravenously at either 100 or 500 ng/kg, and the blood pressure drop (within 10 sec.) and recovery time required to reach the pre-injection blood pressure level are measured. At 100 ng/kg, a 30% decrease in blood pressure and a 3 to 4 minute recovery time are observed, whereas at 500 ng/kg, a 52% decrease in blood pressure and a 10 minute recovery time are observed. In order to measure the effectiveness of a compound for both the inhibition of blood pressure decreases and shortening of the recovery time, the test compound is administered intravenously over a range of between 5 and 7 dosage levels (1 or 2 test animals per dose) and between 1 and 5 minutes prior to the introduction of PAF to generate an $ED_{50}$, Yet even still further, the compounds of formula I are useful as inhibitors of PAF-induced ischemic intestinal necrosis, which property was measured in accordance with the following test (Test E):

Following essentially the procedure of F. Gonzalez-Crussi and W. Hsueh published in J. Amer. Pathol., 112, pgs. 127-135 (1983), male Sprague-Dawley rats, weighing approximately between 260 and 300 g, are anesthetized and their carotid arteries cannulated and connected to a blood pressure transducer and recorder. The test compound is introduced into a cannula inserted into the jugular vein at a time 10 minutes prior to the administration of PAF. The abdomen is then incised along the midline and 2 $\mu$g of PAF or 20 $\mu$g of LPS (lipopolysaccharide) immediately followed by 1 $\mu$g of PAF are injected into the abdominal aorta at the level of the renal artery. The abdominal incision is then covered with saline-moistened gauze and the intestine exposed and examined periodically up to 2 to 3 hours prior to sacrifice. Into the jugular vein is then injected 5 ml of 2% Evans Blue to assess the degree of intestinal perfusion. Blocks of intestinal tissue are then taken for microscopic examination to determine either the extent of necrosis or to verify the absence of necrosis when inhibited by the test compound. Microscopic changes in the intestine are assessed by hematoxylin and eosin staining. The test compound is assessed for its ability to alleviate or prevent the development of gross and microscopic lesions and may be expressed in terms of the number of animals in which inhibition is observed relative to the control (taken to be 100%).

Yet even more still further, the compounds of formula I are useful as inhibitors of PAF-mediated, endotoxin-induced lung injury and, analogously, endotoxin-induced-septic shock and adult respiratory distress syndrome. The ability of the compounds of formula I to inhibit PAF-mediated, endotoxin-induced lung injury can be measured in accordance with the test presented by S. Chang at the 2nd International Conference on *Platelet Activating Factor and Structurally Related Alkyl Ether Lipids* in Gatlinburg, Tenn. on Oct. 26-29, 1986 (Test F).

Based on previous reports that lung tissue and blood PAF increaased in endotoxin-treated rats, it was determined that the intraperitoneal administration of 2 mg/kg of endotoxin (S. enteritidis) causes acute lung injury, as assessed by the extravascular accumulation of water and $^{125}$I-albumin in perfused lungs isolated from rats ninety minutes following in vivo endotoxin treatment. Thus, the wet lung/body weight ratio (as an index of lung water content) increases from 5.35±0.48 to 8.26±0.36 and the albumin leak index increases from 0.46±0.09 to 1.01±0.07. In order to measure the effectiveness of a compound as an inhibitor of endotoxin-induced lung injury, the test compound is administered intraperitoneally prior to the in vivo endotoxin treatment.

The ability of the compounds of formula I to inhibit PAF-mediated, endotoxin-induced septic shock can be measured in accordance with the test presented by C. N. Sessler, et al at the Annular Meeting of the American Federation for Clinical Research in New Orleans, La. during January 1987.

All sheep are prepared for testing employing the Chronic Sheep Lung Lymph preparation which is well documented in the literature, with the modifications that chronic tracheostomies are performed on the test animals and pleural pressure catheters inserted at the time of the initial surgery. All catheters are brought to the outside through stab wounds in the skin, the chest is closed and the test animals are allowed to recover for several days until they appear healthy and lung lymphs are free of blood before experiments are commenced.

In order to measure the effectiveness of a compound as an inhibitor for some of the important hemodynamic effects of endotoxin on septic shock, 1.3 μg/kg of endotoxin or saline is administered to groups of test animals intravenously over a 30 minute period and 20 mg/kg of the test compound or saline is administered intravenously over a five-hour period. The pulmonary arterial pressure (PAP), cardiac output (CO) and partial oxygen pressure ($PO_2$) are monitored continuously over the five-hour period.

The ability of the compounds of formula I to inhibit PAF-mediated, endotoxin-induced adult respiratory distress syndrome can be measured in accordance with the test presented by B. W. Christman, et al at the Annual Meeting of the American Thoracic Society and American Lung Association on May 10th–13th 1987.

In order to measure the effectiveness of a compound as an inhibitor of some of the important hemodynamic effects of endotoxin on adult respiratory distress syndrome, 0.5 ug/kg of *E. coli* endotoxin over a 20 minute period, 20 mg/kg/hr of the test compound for 6 hours, or 0.5 ug/kg of *E. coli* endotoxin 1 hour after commencing 20/kg/hr of the test compound for 6 hours, are administered to groups of test animals intravenously. The pulmonary arterial pressure (PAP), dynamic compliance (DC) of the lungs and lung lymph flow (LLF) are monitored continuously over a five-hour period.

The compounds of formula I, and their pharmaceutically acceptable acid addition salts, may be combined with one or more pharmaceutically acceptable carriers and, optionally, one or more other conventional pharmaceutical adjuvants and administered orally in the form of tablets, dispersible powders, granules, capsules, elixirs, suspensions and the like or parenterally in the form of sterile injectable solutions or suspensions. The compositions may be prepared by conventional means.

The precise dosage of a compound of formula I, or a pharmaceutically acceptable acid addition salt thereof, to be employed for inhibiting platelet activating factor (PAF) depends upon several factors including the host, the nature and the severity of the condition being treated, the mode of administration and the particular compound employed. However, in general, satisfactory inhibition or antagonism of platelet activating factor is achieved when a compound of formula I, or a pharmaceutically acceptable acid addition salt thereof, is administered orally at a daily dosage of 0.05–100, preferably 0.1–30 mg/kg body weight or, for most larger primates, a daily dosage of 1–500 mg, preferably 1–50 mg. A typical oral dosage is 5 mg, three times a day.

As with the PAF inhibition use, the precise dosage of a compound of formula I, of a pharmaceutically acceptable acid addition salt thereof, to be employed in treating PAF-mediated bronchoconstriction and extravasation, PAF-induced hypotension, PAF-involved ischemic bowel disease and PAF-mediated, endotoxin-induced lung injury depends upon several factors including the host, the nature and severity of the condition being treated, the mode of administration and the particular compound employed. However, in general, satisfactory inhibition or antagonism of PAF-mediated bronchoconstriction and extravasation, PAF-induced hypotension, PAF-induced ischemic bowel disease and PAF-mediated, endotoxin-induced lung injury is achieved when a compound of formula I, or a pharmaceutically acceptable acid addition salt thereof, is administered orally at a daily dosage of 0.2–100, preferably 0.2–50 mg/kg body weight or, for most larger primates, a daily dosage of 100–2000 mg, preferably 10–350 mg. A typical oral dosage is 50 or 100 mg, two or three times a day.

Regardless of use, a small dosage is gradually increased until the optimal dosage for the host under treatment is determined. For administration by injection, a dosage somewhat lower than would be used for oral administration of the same compound to the same host having the same condition is usually employed.

The compounds of formula I, and their pharmaceutically acceptable acid addition salts, may be formulated into such pharmaceutical compositions containing an amount of the active substance that is effective for inhibiting PAF, in treating PAF-mediated bronchoconstriction and extravasation, in treating PAF-induced hypotension, in treating ischemic bowel disease or in treating PAF-mediated, endotoxin-induced lung injury, such compositions in unit dosage form and such compositions comprising a solid pharmaceutically acceptable carrier.

Tablets and capsules containing the ingredients indicated below may be prepared by conventional techniques and are useful as platelet activating factor inhibitors. The tablet may be administered once or twice a day whereas the capsule is suitably administered three times a day.

| Ingredients | Weight (mg) tablet | Weight (mg) capsule |
|---|---|---|
| compound of formula I, e.g. the compound of Example 4 | 5 | 5 |
| tragacanth | 10 | — |
| lactose (spray-dried) | 257.5 | 95 |
| corn starch | 15 | — |
| talcum | 10 | — |
| magnesium stearate | 2.5 | — |
| Total | 300.0 | 100 |

The following are representative of tablets and capsules which may be prepared by conventional means and are useful in treating PAF-mediated bronchoconstriction and extravasation, PAF-induced hypotension, PAF-involved ischemic bowel disease and PAF-mediated, endotoxin-induced lung injury. The tablet and the capsule may be suitably administered two or three times a day.

| Ingredients | Weight (mg) tablet | capsule |
|---|---|---|
| compound of formula I, e.g., the compound of Example 4 | 50 | 50 |
| tragacanth | 10 | — |
| lactose (spray-dried) | 212.5 | 100 |
| cornstarch | 15 | — |
| talcum | 10 | — |
| magnesium stearate | 2.5 | — |
| Total | 300.0 | 150.0 |

The following examples show representative compounds encompassed by this invention and their synthesis. However, it should be clearly understood that they are for purposes of illustration only.

EXAMPLE 1

2,5-bis(3,4,5-Trimethoxyphenyl)cyclopent-2-enone

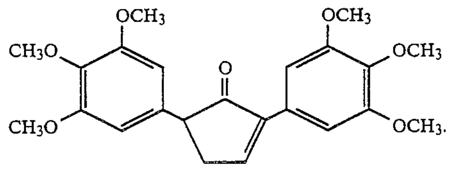

(a) Preparation of 2-(3,4,5-trimethoxyphenylmethyl)-1,3-dithiane

To a solution of 26.7 g of 1,3-dithiane in 222 ml of tetrahydrofuran which has been cooled to −78° C. was added over a period of 15 minutes, 137 ml of 1.7M solution of tetra-butyl lithium in pentane. The resultant mixture was then stirred for 45 minutes, while maintaining the temperature at −78° C., after which time it was warmed to 0° C. The mixture was then added to an ice-cold solution of 48.0 g of 3,4,5-trimethoxybenzyl chloride in 222 ml of tetrahydrofuran over a period of 20 minutes, after which time it was stirred for an additional 90 minutes at 0° C. 50 ml of water was then carefully added and the tetrahydrofuran was removed by evaporation at a temperature below 40° C. The resultant white slurry was then extracted with a mixture of methylene chloride and water. The organic layer was then evaporated and the crude product was washed with petroleum ether to yield a white solid.

(b) Preparation of 2,2-bis(3,4,5-trimethoxyphenylmethyl)-1,3-dithiane

To a solution of 46.3 g of the compound prepared in (a) above in 230 ml of tetrahydrofuran at 0° C. was added, over a period of 20 minutes, 99.6 ml of a 1.7M solution of tert.-butyl lithium in pentane. The resultant mixture was then stirred for 20 minutes, after which time 34.9 g of 3,4,5-trimethoxybenzyl chloride in 150 ml of tetrahydrofuran at 0° C. was added over a period of 15 minutes. The reaction mixture was then stirred for 45 minutes, while the temperature was maintained at 0° C., and then 100 ml of water was carefully added. The resultant slurry was then extracted with a mixture of ethyl acetate and water and dried. The organic layer was then evaporated and the crude product was washed with diethyl ether to yield a solid.

(c) Preparation of 1,3-bis(3,4,5-trimethoxyphenyl)acetone

A solution of 72 g of the compound prepared in (b) above in 96% aqueous methanol was heated to 40° C., after which time 50 ml of iodomethane was added. The reaction mixture was then stirred for 24 hours, while the temperature was maintained at 40° C. The solvent was then evaporated to give an oily residue which was crystallized from a mixture of ethyl acetate and petroleum ether to yield a solid.

(d) Preparation of 1-allyl-1,3-bis(3,4,5-trimethoxyphenyl)acetone

To a solution of lithium diisopropylamide (prepared from the addition of 38.2 ml of a 1.7M solution of tert.-butyl lithium in pentane to 9.53 ml of diisopropylamine in 100 ml of tetrahydrofuran at −10° C.) which was cooled to −78° C. was slowly added 24.1 g of the compound prepared in (c) above in 450 ml of tetrahydrofuran. The resultant mixture was then stirred for 45 minutes, while maintaining the temperature of −78° C., after which time it was cannulated into a solution of 159 ml of allyl bromide in 244 ml of tetrahydrofuran at −78° C. over a period of 90 minutes. The reaction mixture was then stirred for an additional 30 minutes at −78° C., after which time it was allowed to warm to room temperature. 150 ml of water was then added and the tetrahydrofuran was removed by evaporation at 40° C. The crude residue was then extracted with a mixture of ethyl acetate and water and dried, after which time the organic fraction was evaporated to yield a solid.

(e) Preparation of 3,5-bis(3,4,5-trimethoxyphenyl)-4-oxo-pentanol

To a solution of 27.5 g of the compound prepared in (d) above in 640 ml of a mixture of tetrahydrofuran and water (in a 2:1 ratio) was added 9 ml of a 2.5% solution of osmium tetraoxide in tert.-butanol. The reaction mixture was then allowed to stir at room temperature until it darkened to a black opaque mixture, after which time 82.07 g of sodium metaperiodate was added. The resultant mixture was then stirred at room temperature for 20 hours, after which time it was filtered and the solvent was removed by evaporation to yield a residue that was extracted with a mixture of ethyl acetate and water. The organic layer was evaporated and the resultant residue was chromatographed on silica gel employing a mixture of methylene chloride and ethyl acetate in a ratio of 8:1 as the eluent to yield a solid.

Preparation of the title compound

A mixture of 3.65 g of the compound prepared in (e) above, 3.04 g of dibenzo-18-crown-6 and 0.68 g of powdered sodium hydroxide in 845 ml of benzene was stirred for 20 minutes at room temperature and for 2 hours at 80° C. The mixture was then washed with 300 ml of 1N hydrochloric acid and the aqueous layer was then washed with methylene chloride. The combined organic fractions were then washed with a saturated sodium chloride solution, dried and evaporated. The crude residue was then flash chromatographed on silica gel and eluted successively with methylene chloride and then, by slowly adding ethyl acetate, mixtures of methylene chloride and ethyl acetate until the latter was present at a level of 10% of the mixture. The resultant product was then recrystallized from ethanol to yield the title compound, m.p. 119°-120° C.

| | | |
|---|---|---|
| Test A | $IC_{50}$ | 6 uM |
| Test B | $ED_{50}$ | 1.0 mg/kg (i.a.) |
| Test C | $ED_{50}$ | 1.0 mg/kg (i.a.) |

EXAMPLE 2

2,5-bis(3,4,5-Trimethoxyphenyl)cyclopentanone

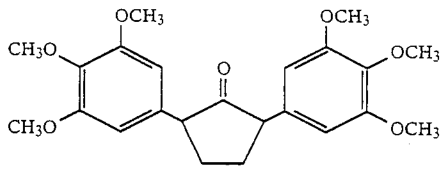

A mixture of 2.38 g of the compound of Example 1 as a 0.1M ethanol solution and 900 mg of 10% palladium on carbon was stirred, under a 50 psi. atmosphere of hydrogen gas, for 17 hours. The mixture was then filtered through Celite and the crude residue was flash chromatographed on silica gel employing ethyl acetate as the eluent to yield the title compound.

| | | |
|---|---|---|
| Test A | $IC_{50}$ | 0.9 uM |
| Test B | $ED_{50}$ | >20 mg/kg. (p.o.) |
| Test C | $ED_{50}$ | >20 mg/kg. (p.o.) |

EXAMPLE 3

2,5-bis(3,4,5-Trimethoxyphenyl)cyclopentanol

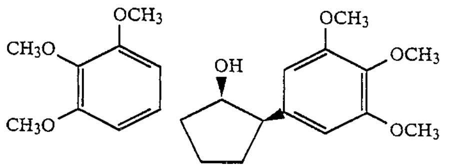

1α, 2α, 5βisomer

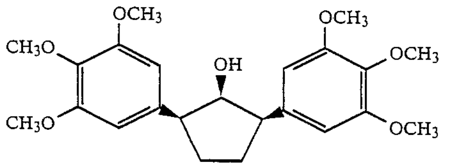

1α, 2α, 5αisomer

To a solution of 2.26 g of the compound of Example 2 in 54 ml of tetrahydrofuran which was cooled to −78° C. was added 14.5 ml of a 1.5M solution of diisobutylaluminum hydride in toluene. The reaction mixture was then stirred for 2 hours, while maintaining the temperature at −78° C., after which time it was warmed to room temperature. The mixture was then stirred for an additional 22 hours, after which time it was poured into a mixture of 100 ml of ethyl acetate and 100 ml of a saturated aqueous ammonium chloride solution. The resultant mixture was then filtered through Celite and the filtrate was extracted with a mixture of ethyl acetate and water. The organic layers were then combined, dried and evaporated to afford the crude residue which was chromatographed on silica gel employing a mixture of hexane and isopropyl alcohol in a ratio of 3:1 as the eluent to yield the 1α, 2α, 5β and 1α, 2α, 5α isomers of the title compound, the former of which had a m.p. of 126°–128° C., and the latter of which had a m.p. of 138°–140° C.

| 1α, 2α, 5β isomer | | | 1α, 2α, 5α isomer | | |
|---|---|---|---|---|---|
| Test A | $IC_{50}$ | 4.7 uM | Test A | $IC_{50}$ | 2.8 uM |
| Test B | $ED_{50}$ | >20 mg/kg(p.o.) | Test B | $ED_{50}$ | ~20 mg/kg (p.o.) |
| Test C | $ED_{50}$ | >20 mg/kg(p.o.) | Test C | $ED_{50}$ | >20 mg/kg (p.o.) |

EXAMPLE 4

(1α,2α,5β)-2,5-bis(Trimethoxyphenyl)-1-methoxy cyclopentane

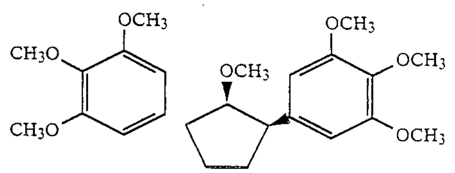

528 mg of a suspension of 60% sodium hydride in oil was washed with pentane and to the washed suspension was added 8 ml of tetrahydrofuran. The resulting suspension was cooled to 0° C. and to the cooled suspension was added 690 mg of the 1α, 2α, 5β isomer of Example 3 in 8.5 ml of tetrahydrofuran. The reaction mixture was then stirred for 30 minutes, while the temperature was maintained at 0° C., after which time 1.03 ml of iodomethane was added. The resultant mixture was then stirred for 30 minutes, while the temperature was maintained at 0° C. and, after warming the mixture to 40° C., it was stirred for an additional 2.5 hours, after which time it was extracted with a mixture of ethyl acetate and water and dried. The organic fraction was then evaporated and the crude residue obtained was chromatographed on silica gel employing a mixture of petroleum ether and ethyl acetate in a ratio of 2.:1 as the eluent to yield the title compound, m.p. 98°–100° C.

| | | |
|---|---|---|
| PAIA test | $IC_{50}$ | 0.88 uM |
| Test A | $IC_{50}$ | 0.1 um |
| Test B | $ED_{50}$ | 0.5 mg/kg (i.a.) |
| Test C | $ED_{50}$ | 0.4 mg/kg (i.a.) |
| Test D | $ED_{50}$ | 0.12 mg/kg (i.v.) |

EXAMPLE 5

(1α,2α,5α)-2,5-bis(Trimethoxyphenyl)-1-methoxy cyclopentane

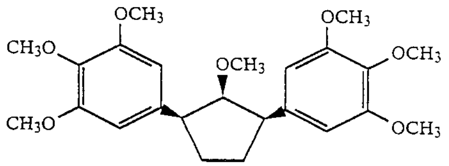

320 mg. of a suspension of 60% sodium hydride in oil was washed with pentane and to the washed suspension was added 8 ml of tetrahydrofuran. The resulting suspension was cooled to 0° C. and to the cooled suspension was added 4.8 mg of the 1α, 2α, 5α isomer of Example 3 in 8.5 ml of tetrahydrofuran. The reaction mixture was then stirred for 30 minutes, while the temperature was maintained at 0° C., after which time 1.62 ml of iodomethane was added. The resultant mixture was then stirred for 30 minutes, while the temperature was maintained at 0° C. and, after warming the mixture to 40° C., it was stirred for an additional 2.5 hours, after which time it was extracted with a mixture of ethyl acetate and water and dried. The organic fraction was then evaporated and the crude residue obtained was chromatographed on silica gel employing a mixture of petroleum ether and ethyl acetate in a ratio of 3:1 as the eluent to yield the title compound, m.p. 133°-135° C.

PAIA test—$IC_{50}$—22 uM

EXAMPLE 6

(1α,5α)-2,5-bis(3,4,5-Trimethoxyphenyl)cyclopent-2-enol

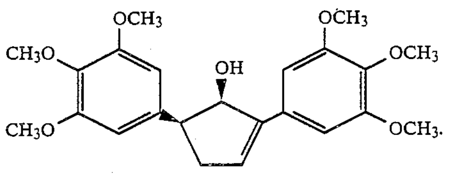

To a solution of 0.30 g of the compound of Example 1 in 7.25 ml of tetrahydrofuran which was cooled to −78° C. was added 1.69 ml of a 1.5M solution of diisobutylaluminum hydride in toluene. The reaction mixture was then stirred for 4 hours, while the temperature was maintained at −78° C., after which time it was warmed to room temperature and then extracted with dichloromethane and 1N hydrochloric acid. The organic fraction was then washed successively with water, a saturated aqueous sodium bicarbonate solution and a saturated aqueous sodium chloride solution, after which time it was dried and evaporated to yield a residue which was chromatographed on silica gel employing a mixture of dichloromethane and ethyl acetate in a ratio of 4:1 as the eluent. The product obtained was then recrystallized from ethyl acetate and petroleum ether to yield the title compound, m.p. 174°-177° C.

Test A—$IC_{50}$—<100 uM

EXAMPLE 7

(4α,5α)-1,5-bis(3,4,5-Trimethoxyphenyl)-5-methoxy cyclopentene

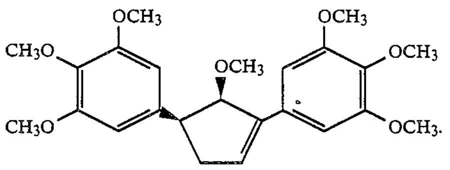

122 mg of a 60% suspension of sodium hydride in oil was washed with pentane and to the washed suspension was added 8 ml of tetrahydrofuran. The resulting suspension was cooled to 0° C. and to the cooled suspension was added 127.3 mg of the compound of Example 6 in 8.5 ml of tetrahydrofuran. The reaction mixture was then stirred for 30 minutes, while the temperature was maintained at 0° C., after which time 0.23 ml of iodomethane was added. The resultant mixture was then stirred for 30 minutes, while the temperature was maintained at 0° C. and, after warming the mixture to 40° C., it was stirred for an additional 2.5 hours, after which time it was extracted with a mixture of ethyl acetate and water and dried. The organic fraction was then evaporated and the crude residue obtained was chromatographed on silica gel employing a mixture of petroleum ether and ethyl acetate in a ratio of 2:1 as the eluent. The product obtained was then recrystallized from ethyl acetate and petroleum ether to yield the title compound, m.p. 136°-137° C.

| | | |
|---|---|---|
| PAIA test | $IC_{50}$ | 12.2 uM |
| Test A | $IC_{50}$ | 1.1 uM |
| Test B | $ED_{50}$ | <1.0 mg/kg (i.a.) |
| Test C | $ED_{50}$ | <1.0 mg/kg (i.a.) |

EXAMPLE 8

2,5-bis(3,4,5-Trimethoxyphenyl)cyclopentanone, O-methyloxime

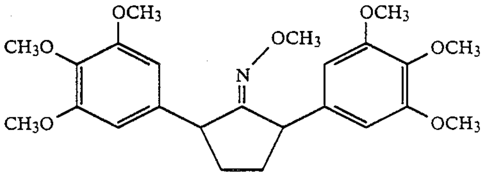

To a solution of 470 mg of the compound of Example 2 in 7.53 ml of pyridine was added 563 mg of methoxyamine hydrochloride. The reaction mixture was stirred at 70° C. for 3 hours, after which time it was extracted with a mixture of dichloromethane and 1N hydrochloric acid. The organic fraction was then dried and evaporated and the crude residue obtained was chromatographed on silica gel employing a mixture of petroleum ether and ethyl acetate in a ratio of 1:1 as the eluent to yield the title compound.

EXAMPLE 9

2,5-bis(3,4,5-Trimethoxyphenyl)cyclopentanone, oxime

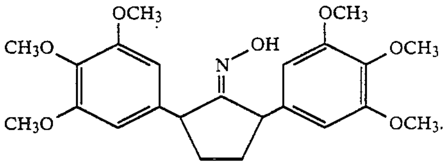

To a solution of 212 mg of the compound of Example 2 in 7.53 ml of pyridine was added 211 mg of hydroxylamine hydrochloride. The reaction mixture was stirred at 70° C. for 3 hours, after which time it was extracted with a mixture of dichloromethane and 1N hydrochloric acid. The organic fraction was then dried and evaporated and the crude residue obtained was chromatographed on silica gel employing a mixture of petroleum ether and ethyl acetate in a ratio of 1:1 as the eluent to yield the title compound.

| | | |
|---|---|---|
| Test A | $IC_{50}$ | 0.45 uM |
| Test B | $ED_{50}$ | 0.87 mg/kg (p.o.) |
| Test C | $ED_{50}$ | 0.75 mg/kg (p.o.) |

EXAMPLE 10

1-Amino-2,5-bis(3,4,5-trimethoxyphenyl)cyclopentane

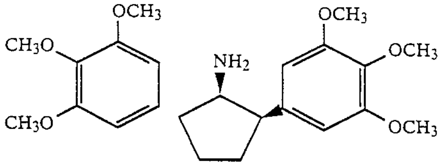

2α, 2α, 5βisomer

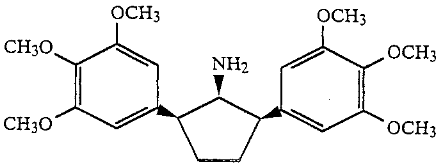

1α, 2α, 5αisomer

To a solution of 267 mg of the compound of Example 8 in 4 ml of tetrahydrofuran which was cooled to −78° C., was added 6.0 ml of a 1M solution of diborane in tetrahydrofuran over a period of 2 minutes. The reaction vessel was then sealed and heated at 50° C. for 16 hours and then at 70° C. for 3 hours, after which time it was cooled to 0° C. The reaction mixture was then poured into 100 ml of a 10% aqueous potassium hydroxide solution and the resultant solution was then heated at reflux for 1 hour, after which time it was cooled and extracted three times with 100 ml of dichloromethane. The combined organic extracts were then washed successively with water and a saturated aqueous sodium chloride solution, after which they were dried and evaporated. The residue was then chromatographed on silica gel employing a mixture of ethyl acetate and petroleum ether in a ratio of 4:1 as the eluent to yield the 1α, 2α, 5β and 1α, 2α, 5α isomers of the title compound, the latter of which had a m.p. of 117°-119° C.

| 1α, 2α, 5β isomer | | | 1α, 2α, 5α isomer | | |
|---|---|---|---|---|---|
| Test A | $IC_{50}$ | 2.7 uM | Test A | $IC_{50}$ | 22 uM |

What is claimed is:

1. A compound of formula Ib:

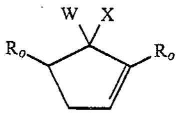

Ib where

W is hydrogen; $C_1$-$C_5$alkyl or $C_3$-$C_6$alkenyl; and

X is $OR_1$ and $SR_1$ where $R_1$ is hydrogen, $C_1$-$C_5$alkyl or $C_3$-$C_6$alkenyl; or $NR_1R_1$, where each $R_1$, independently, is as defined above; with the proviso that when W is other than hydrogen, then X is $OR_1$;

or W and X, together with the carbon atom to which they are attached, are C═O or C═$NOR_1$, where $R_1$ is as defined above; and each Ro, independently, is a group of the formula

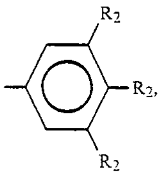

where each $R_2$ is, independently, hydrogen; $NO_2$; halo; $OR_3$, where $R_3$ is $C_1$-$C_5$alkyl; $SR_4$; $SOR_4$; $SO_2R_4$; $NHSO_2R_4$; $NR_4R_4$; $NR_4SO_2R_4$ or $NHSO_2NR_4R_4$, where each $R_4$ is $C_1$-$C_5$alkyl or $C_3$-$C_6$ alkenyl; with the proviso that only one $R_2$ can be a significance selected from hydrogen, $NO_2$, halo, $SR_4$, $SOR_4$, $SO_2R_4$, $NHSO_2R_4$, $NR_4R_4$, $NR_4SO_2R_4$ and $NHSO_2NR_4R_4$, or a pharmaceutically acceptable acid addition salt thereof.

2. A compound according to claim 1 formula Ib':

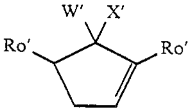

Ib' where

W' is hydrogen or $C_1$-$C_5$alkyl;

and X' is $OR_1'$ or $NR_1'R_1'$ where $R_1'$ is hydrogen or $C_1$-$C_5$alkyl; with the proviso that when W' is other than hydrogen, then X' is $OR_1'$;

or W' and X', together with the carbon atom to which they are attached, are C═O or C═$NOR_1'$, where $R_1'$ is as defined above;

and each $R_o'$, independently, is a group of the formula

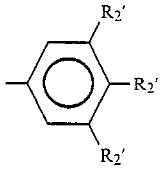

where $R_3$ is $C_1$-$C_5$alkyl; or a pharmaceutically acceptable acid addition salt thereof.

3. A compound according to claim 2 of formula Ib'':

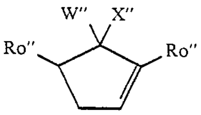

Ib'' where

W'' is hydrogen or $C_1$-$C_3$alkyl;

and X'' is $OR_1''$ or $NR_1''R_1''$ where $R_1''$ is hydrogen or $C_1$-$C_3$alkyl; with the proviso that when W'' is other than hydrogen, then X'' is $OR_1''$;

or W'' and X'', together with the carbon atom to which they are attached, are C═O or C═$NOR_1''$, where $R_1''$ is as defined above;

and the $R_o''$'s are the same and represent a group of the formula

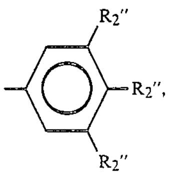

$OR_3'$ where $R_3'$ is $C_1$–$C_3$alkyl; or a pharmaceutically acceptable acid addition salt thereof.

4. A compound according to claim 3 of formula Ib''':

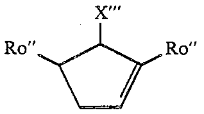

Ib''' where

X''' is $OR_1''$ where $R_1''$ is as defined in claim 3; and the $R_o'''$s are the same and represent a group of the formula

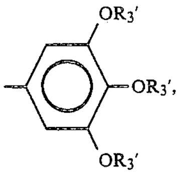

as defined in claim 3; or a pharmaceutically acceptable acid addition salt thereof.

5. A compound according to claim 3 having the formula

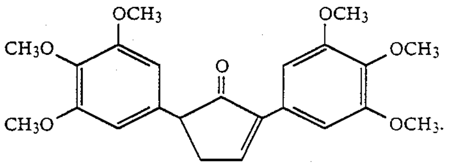

6. A compound according to claim 4 having the formula

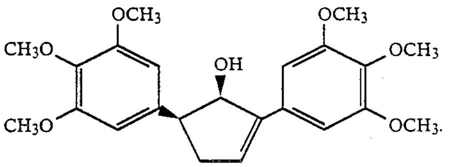

7. A compound according to claim 4 having the formula

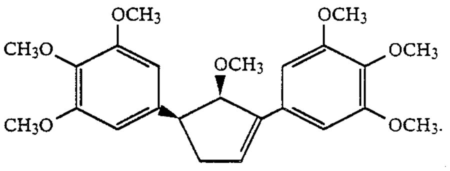

8. A pharmaceutical composition useful in inhibiting PAF-induced blood platelet aggregation, PAF-mediated bronchoconstriction and extravasation, PAF-induced hypotension, PAF-induced ischemic bowel disease and PAF-mediated, endotoxin-induced lung injury comprising a pharmaceutically acceptable carrier and a therapeutically effective amount of a compound according to claim 1.

* * * * *